United States Patent
Boender

(10) Patent No.: US 10,531,966 B2
(45) Date of Patent: Jan. 14, 2020

(54) PROSTHETIC JOINTS

(71) Applicants: Jacob Quintus Laurence Anthony Boender, Marcham, Oxfordshire (GB); Jennifer Boender, Marcham, Oxfordshire (GB)

(72) Inventor: Jacob Quintus Laurence Anthony Boender, Marcham (GB)

(*) Notice: Subject to any disclaimer, the term of this patent is extended or adjusted under 35 U.S.C. 154(b) by 0 days.

(21) Appl. No.: 15/069,856

(22) Filed: Mar. 14, 2016

(65) Prior Publication Data

US 2016/0296347 A1    Oct. 13, 2016

(30) Foreign Application Priority Data

Mar. 13, 2015    (GB) .................................. 1504242.7

(51) Int. Cl.
    *A61F 2/64*    (2006.01)
    *A61F 2/50*    (2006.01)
    *A61F 2/74*    (2006.01)

(52) U.S. Cl.
    CPC ...... *A61F 2/642* (2013.01); *A61F 2002/5006* (2013.01); *A61F 2002/745* (2013.01)

(58) Field of Classification Search
    CPC .. A61F 2/64; A61F 2/642; A61F 2/644; A61F 2/646; A61F 2002/6818
    See application file for complete search history.

(56) References Cited

U.S. PATENT DOCUMENTS

| | | | | |
|---|---|---|---|---|
| 4,215,441 A | * | 8/1980 | Wilson | A61F 2/605 623/31 |
| 4,488,320 A | * | 12/1984 | Wilson | A61F 2/605 623/29 |
| 6,764,520 B2 | | 7/2004 | Deffenbaugh et al. | |
| 6,902,585 B2 | | 6/2005 | Hikichi | |
| 8,915,969 B2 | | 12/2014 | Boender | |
| 2002/0177905 A1 | * | 11/2002 | Yih | A61F 2/88 623/23.75 |

(Continued)

FOREIGN PATENT DOCUMENTS

| | | |
|---|---|---|
| EP | 2478875 A2 | 7/2012 |
| GB | 2328160 A | 2/1999 |
| GB | 2464620 A | 4/2010 |

OTHER PUBLICATIONS

Hugh Herr, Ari Wilkinfeld, User-adaptive control of a magnetorheological prosthetic knee, Industrial Robot: An International Journal, Feb. 1, 2003 MCB Univ. Press, Bradford—ISSN 0143-991X; vol. 30, Nr:1, pp. 42-55.

*Primary Examiner* — Bruce E Snow
(74) *Attorney, Agent, or Firm* — Anderson Gorecki LLP

(57) ABSTRACT

The present invention relates to a prosthetic leg for those having a femoral amputee, namely those having an above the knee stump, where certain movements can be difficult to perform. Known prosthetic knee joints that are weight-activated cannot substantially assist short-stumped individuals. The weight placed on the toe will typically cause disengagement of any stance mode there otherwise might be. The invention provides a solution to the problems addressed above. The present invention seeks to provide an improved mechanically operated prosthesis for a femoral amputee. The invention also provides an improved electrically-operated prosthesis for a transfemoral amputee.

14 Claims, 9 Drawing Sheets

(56) References Cited

U.S. PATENT DOCUMENTS

2012/0101599 A1\* 4/2012 Olafsson ................ F16C 23/04
 623/39
2013/0261766 A1 10/2013 Langlois et al.
2015/0005686 A1\* 1/2015 Kazerounian ......... A61F 5/0123
 602/16
2015/0230962 A1\* 8/2015 Auberger ............. A61F 5/0123
 602/26

\* cited by examiner

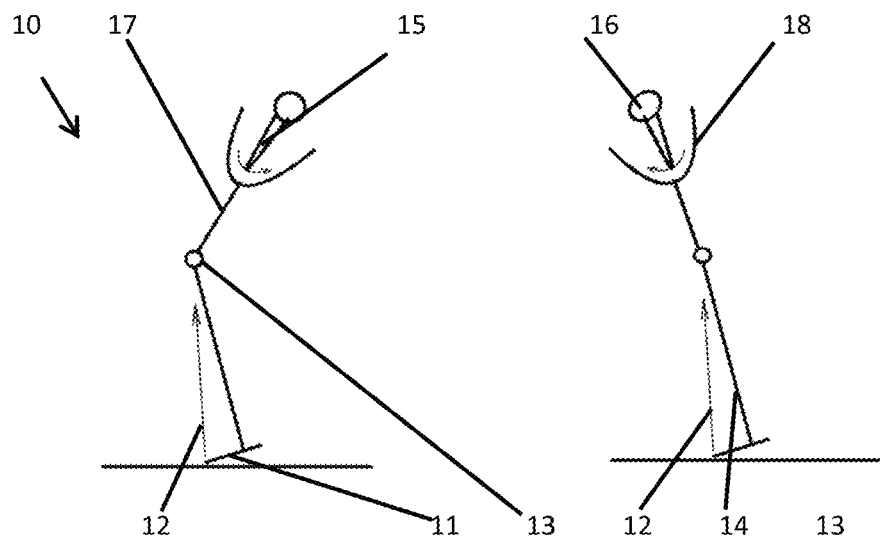
Figure 1i (prior art)          Figure 1ii (prior art)
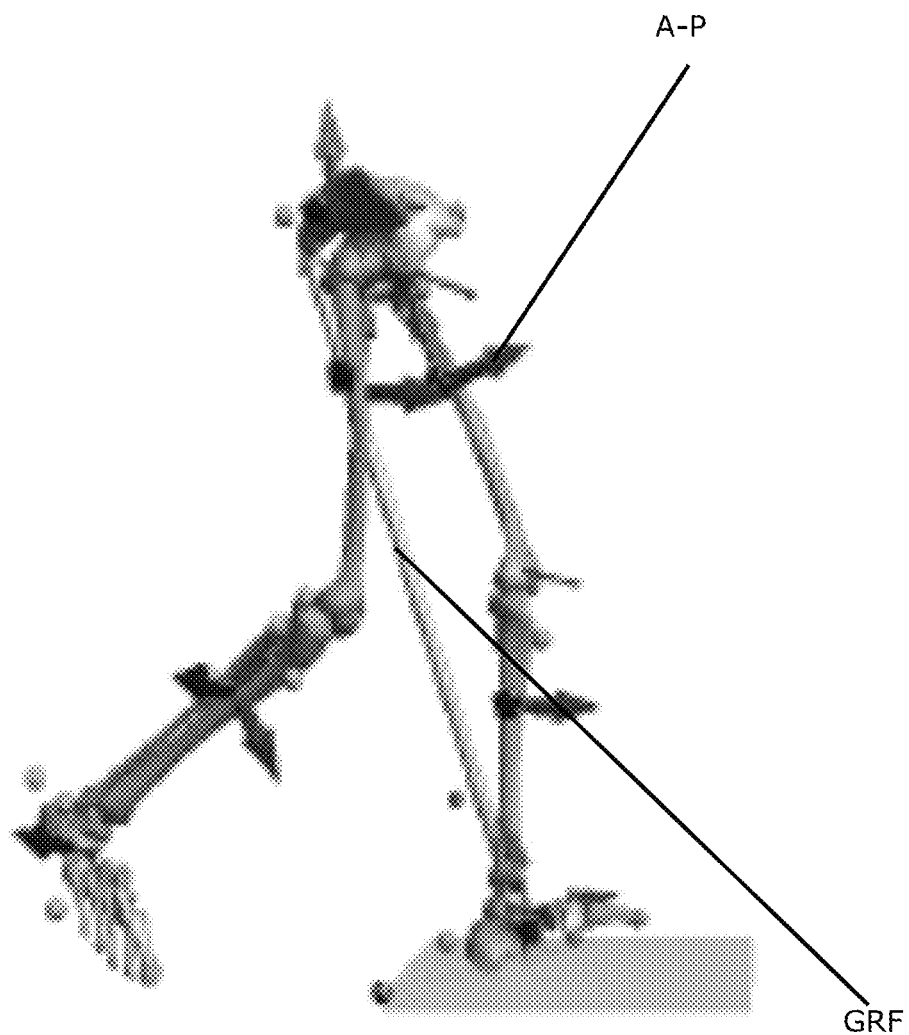
Figure 1iii Figure 4i (prior art)  Figure 4ii (prior art)  Figure 4iii Prior art

PROSTHETIC JOINTS

CROSS-REFERENCE TO RELATED APPLICATIONS

This application is a continuation of UK patent application serial number GB1504242.7 titled "IMPROVEMENTS IN OR RELATING TO PROSTHETIC JOINTS" which was filed on Mar. 13, 2015, the entire specification of which is incorporated herein by reference in its entirety.

BACKGROUND OF THE INVENTION

Field of the Art

The present invention relates generally to prosthetic legs and, in particular to modular knee joints for prosthetic legs. In particular the present invention relates to a prosthetic leg for those having had a transfemoral amputation, namely those having an above the knee stump, and particularly to a prosthetic leg for transfemoral amputees for whom 50% or more of their femur has been amputated. The present invention also lends itself to prosthetic modularity.

Discussion of the State of the Art

Amputees who use a lower limb prosthesis equipped with a knee joint, find certain movements difficult to perform. For example, the fact that the prosthesis comprises a mechanical apparatus performing the duty of the joint that is substantially distal to the hip can induce a lack of balance. Indeed, patients having a substantial reduction in femoral length will suffer greatly since the prosthetic attachment typically has a hollow region, a socket, in which to insert the remaining length of thigh, the stump; the stump will bear upon the distal aspect of the femur and the femoral lever action will be reduced, in correspondence with the reduction in length. Indeed the pressures can become unbearably high-often resulting in an occurrence of friction burns arising through sliding contact with the prosthesis stump. In fact the length to width ratio of the stump can come close to 1:1 as opposed to a 2:1 or 3:1 as is typical for a normal human femur. It will be understood that the center of mass of a state of the art knee mechanism in a lower limb prosthesis is distal to the same knee center, which allows for a universal application of the prosthetic joint; indeed, any aspect of such a joint proximal to the knee center is kept as short as possible to support a wide as possible commercial and clinical application independent of femoral stump length. Naturally there is a transition across length, but practice bears out that a "heavy" prosthesis is beneficial to the long-femured transfemoral amputee for reasons of body mass symmetry, and very cumbersome and uncomfortable for the short-femured transfemoral amputee, a distinct sub-class of transfemoral amputee the disclosure is made.

In the provision of an above-the-knee prosthesis with locking and/or yield characteristics, one can employ mechanical, pneumatic, or hydraulic devices. There are five distinct categories of prosthetic mechanisms available for those with knee and above knee limitations. The primary design—as in the most common type—comprises a polycentric mechanism wherein the virtual center of rotation is well above the anatomical knee axis—the mechanical apparatus, and its center of mass (approx. 850 gr, 1½ lb.), is distal to the anatomical knee center. Another prosthetic mechanism is the hydraulic swing'n'stance ("SNS") mechanism developed in the late 1960's by Hans Mauch. This design operates in a stance phase of operation in a default mode; the mechanism is brought into swing on hyperextension of the femur. The Mauch SNS has an internal mechanism where the overstretching of a hydraulic assembly lifts a valve-operating member and enables the leg to operate in a low resistance swing phase. This, again, is enabled at a point distal to the anatomical joint center. A further prosthetic type comprises a weight-activated type of knee joint such as described in GB2464620 (Boender). A fourth type of prosthesis is exemplified by a number of relatively expensive, external battery powered, electromechanical knee joints having sensors and dampers operating under software control for control of the same joint function, albeit with a relatively high mass (approx. 1.4 kg, 3 lb.), distal to the knee center. A fifth type of prosthesis is the fluidic controlled knee joint, wherein by means of fluid flow and mechanical linkages, appropriate negative feedback to the control of movement can be realized, which suffers the same penalty of a relatively high mass, distal to the knee center. It will be readily understood that the more distal and the larger the mass of the knee joint becomes, the effects of unwanted reactive pressures which act on the distal end of a short amputation stump are exacerbated, even at low ambulatory speeds.

The prevalence of prostheses is increasing as people are living longer and in view of the provision of prostheses in respect of previously life threatening injuries and conditions arising from accidents where limb injuries occur are and improvements, for example, in diabetic management, become more widely available. Prostheses manufacturers have adopted certain interoperability standards whereby a modular knee joint from one manufacturer can be replaced with a unit form another manufacturer, meaning that the knee joint is a dismountable and exchangeable part of a whole-leg prosthesis. While each knee joint prosthesis cooperates with other parts of the prosthesis such as the foot in mid-swing, and operable to lower the mass of the user's body down a stair, it is a distinct modular device with a proximal end and a distal end which are the boundaries of the space envelope of the knee joint per se. Naturally a modular joint, as an individual product, has a center of mass and the weight of a modular joint is typically declared in the sales literature and is provided with distributed product. Typical prior art modular knee joints have their center of mass distal to the knee center (or knee axis) about which these are operable. Parts of a prosthesis, such as a foot, shin tube, torque absorbers etc. are referred to as prosthetic components, which are necessary to build a prosthesis, but can be considered separately to the present invention. These components need to be moved throughout space during swing phase of the prosthesis, and the precise movement—with particular reference to the angular relationship between these components relative to the stump attachment device—is controlled by the knee joint. The knee joint has its own center of mass that can be identified in isolation to any housing or exo-skeletal part of the knee joint, which along with the mechanical characteristics of the joint to include aspects such as damping (hydraulic or otherwise), friction (hydraulic or otherwise), position of pivot axis—or axes in the case of a poly-centric joint etc.). For the purposes of scope of disclosure, hip disarticulation prostheses will be understood to count as a special form of short transfemoral amputation prosthesis. Hydraulic knee devices benefit from the liquid being incompressible and can provide friction dependent upon speed; locking and yielding functions can simply be provided by different settings of a variable orifice.

Control of a prosthetic device through the yielding and locking functions of the prosthesis, must have near perfect reliability, particularly on stairs, inclines, and in stumbling situations, in order to prevent accidents. For example, in a weight activated knee joint, a change in posture (or equivalent) is required to apply weight to the joint, whereby to enable the joint to switch from its default free swing mode into a stance mode for weight acceptance, to prevent collapse. Similarly, the default stance joints need to be brought into a low torque or low resistance mode to facilitate the swing phase. Referring to FIGS. 1*i* and 1*ii*, there is shown a simplified view of one type of known prosthesis 10, comprising a thigh member 17—complete with insert, also known as a socket 18, a knee 13 and shin 14, in positions of toe-contact but under different circumstance. FIG. 1*i* shows the leg in stumble mode, where a swing extension movement is interrupted by sudden toe contact with the ground. In an attempt to prevent a fall, the body mass must be shifted to the prosthesis, whereby to allow placement of the sound limb ahead of the body so that the forward momentum of the body will not result in a fall. This figure also shows how the forces pass through the forefoot in stumble mode—which correspond with the forces that pass through the foot in toe-off mode. When a ground reaction force passes slightly posterior to the knee center, then the knee joint will readily bend until movement is arrested. At toe-off, the knee joint will also readily bend as in swinging the leg. In the case of a stumble the knee joint will bend further and collapse, being a most undesirable outcome. Typical state of the art weight activated joints do not have stumble recovery options as in FIG. 1*i*, even though it is clearly desirable for such prostheses to be provided with a stumble recovery mode. Indeed, neither such a mechanism, nor the polycentric mechanism allow any change in bending resistance once the load is on the forefoot/toe. Accordingly, a stumble will certainly lead to a collapse. Notwithstanding this, the short stumped amputee will be bereft of any intrinsic stumble recovery ability, where a long stumped individual could arrest a fall by employing their effectively stronger hip muscles. FIG. 1*ii* shows how forefoot 11, having a ground reaction force 12 acting through the knee 13 and which would otherwise be a poor location for engagement of the stance phase, except that it enables the knee to commence swing action. It will be realized that during normal swing function, a stance resistance would be most undesirable.

Indeed the main body of these joints is typically located distal to the knee axis. It will be appreciated that the short stumped, above knee amputee is not well served by these devices of the prior art, especially those that use a default stance mechanism wherein bodyweight on the forefoot at toe-off is required to release the knee into a swing mode. For example, the need for specific stump movement to drive the prosthesis into swing under a residual toe-load can be too much. Instead a weight activated knee joint is generally found to be preferable, where body weight is usefully employed to stabilize the stance mode, and upon simple removal of body weight defaults to a swing mode.

Any prosthesis will have mass. While one important issue is the effective weight arising from gravity, a more troublesome issue arises upon use and, in particular, upon a forward swing of the prosthesis. Unlike the weight of the prosthesis that remains the same irrespective of distribution of mass, the perception of "weight" in kicking the leg forward with the thighbone is very much dependent on the mass distribution. Those skilled in the art will readily confirm that the inertia of a given mass M that is accelerated by a moment, (that is a force applied perpendicularly at a distance r) is given as $Mr^2$, which means that, if a similar mass is twice the distance away from the source that pushes it, the inertia (or the sensation of its heaviness) is four times as great. In the case of a prosthesis, there will always be a foot of some description that must be at a given distance from the hip, to create the right leg length for balance, body symmetry, and an energy efficient gait. Therefore the location of the mass of the foot cannot be altered, and the only way to reduce the inertia is to reduce the mass of the foot and shoe. The situation for the knee joint is quite different; the location of the center of mass of the knee joint can be brought close to the knee center (by selecting a small joint), and by selecting a small mass (small knee joint) at a cost of losing function such as stumble recovery, yielding under body weight in downstairs walking, because in engineering functionality typically adds mass.

Known prosthetic knee joints that are activated only by the application of weight cannot substantially assist the short stumped individual. The weight placed on the toe, as in toe-off, will typically cause disengagement of any stance mode there otherwise might be. This has to be so, because at toe-off, prior to swing, when residual body weight is on the toe, the knee joint must be free to release for swing, and this condition of weight acceptance is, using known devices, indistinguishable from any attempted weight acceptance during attempted stumble recovery with respect to the knee mechanism. In summary, known prosthetic knee & limb devices are either light weight—a benefit, with meager function or safety—a significant disadvantage, but if the engineering requirements are met—a benefit, the inertial mass of the device is too high for comfort—a significant disadvantage, liable to cause unwanted side effects such as the occurrence of friction burns on the distal stump.

Such prior mechanisms, whether mechanically or electronically controlled and operated, rely upon the application of forces by the prosthesis upon the prosthetic apparatus distal to the knee center, noting that the center of mass of the prosthesis is also distal to the knee center. For example, Yuichi (US2005015156) claims to teach of an above-knee prosthesis that permits a user to control knee flexion or extension and to enable voluntary lock and release of the knee joint, at any angle of bend. Indeed, an objective of Yuichi is to provide a natural gait. The prosthesis to Yuichi comprises a thigh frame assembly that receives a thigh stump; a leg frame assembly operably associated with a foot; a hinge interconnects the assemblies to form an artificial knee joint. A closed hydraulic system provides variable resistance to the bending of the artificial knee joint in correspondence with anterior-posterior (AP) movement of the thigh stump. The AP movement of the thigh stump is conveniently arranged to control a flow rate valve by means of a linkage, sliding or screw assembly. The flow rate control valve varies the resistance provided by the closed hydraulic system: pressing the thigh stump backwards within the thigh frame assembly increases resistance and slows knee bending until the knee locks, while pressing the same forwards decreases resistance and allows the artificial knee joint to yield to outside forces, such as gravity and/or stump thrust, the prosthesis can pivot freely about the knee hinge.

Yuichi operates solely on the AP force vectors present in the hip flexion and extension efforts and all embodiments teach of isolation of AP forces from any axial forces, even when the incline of the sensor is slightly tilted, i.e. not perpendicular to the femoral axis: separation occurs between force vector components in the operating plane of the sensor and force vector components in the plane normal to the operating plane. Confusingly, Yuichi defines "AP" in terms of a plane/direction of operation of the sensor device, which makes the discussion about any tilt of this direction relative to the body immaterial. Also confusingly, Yuichi suggests of control by means of hip musculature (¶45), despite that fact that in real gait, for example, upon heel strike with the ground, a force vector naturally passes posterior to the knee center, with reference to Newton's third law. Due to gravity, a body will constantly maintain contact with the ground; the reaction force arising from the ground is the ground reaction force (GRF). The GRF, along with weight, is an important external force. The GRF is normally determined by means of a force-plate, which comprises four tri-axial force sensors that measure the force acting between the foot and the ground in three axes: transverse (Z), anterior-posterior (X), and vertical (Y). The resultant sum of all the reactions from the ground is equivalent to the sum of the four forces measured by the sensors (for more detail, refer to material relating to Biomechanics course 3150 per "BioMedical Engineering OnLine". The implications of this is that the prosthetic tibia by direction of ground reaction force (GRF) must attempt to move rearwardly with respect to the distal stump, or distal femur slide forward (anteriorly) over the knee apparatus, the GRF vector being shown upon heel touch down of a left leg with reference to FIG. 1$iii$. Thus, in accordance to Yuichi, would cause the knee joint to be in a low resistance mode and collapse would commence. When the artificial limb apparatus allows commencement of partial collapse, the ground reaction force would start to tilt forward in reaction to a thigh extension reflex, and in accordance to Yuichi's teaching the knee would stabilize and due to the body weight sliding backwards relative to the knee axis, the hydraulic resistance would soon increase to its maximum, but not be under useful voluntary control. Indeed, the AP forces to Yuichi are defined relative to the continually moving reference "vertical", corresponding to a longitudinal axis of the femur, in alignment with the coronal plane and this is in contrast with any standard medical reference of the term "AP".

Any claimed voluntary control that is possible with such devices with respect to a level of resistance over knee bending in sitting down does not necessarily become apparent in practice and it is believed that the resistive bending moments will have an "AP" force component equal to the product of the knee bending resist moment and an inverse factor of the distance from hip to knee center, which for a typical male would correspond to the forces arising from half the weight, say 450N (100 lb force). Because the force returned in the sensor device is equal to the pressure the user exerts on it, the user must also provide such levels of force to the sensor device to get a level of resistance. When walking down a stair, the thigh is at approximate 15° relative to vertical, which means that in the time frame of single leg weight bearing, the "AP" force component delivered to the control device is only 25% (sin 15°) of the body weight, meaning that the resistive torque that slows down the descent of the body will permit a g-force of 75%×9.81 to act on the body, which would result in an uncontrolled descent.

In another scenario, where a limb swings through mid-swing, it is known that the bending resistance of the knee must be a maximum at mid-swing, which in terms of such prior devices can only be provided by a posterior force exerted on the knee mechanism in mid-swing to provide this level of knee control consistent with the teachings. This means that the forward swinging thigh must provide a sudden rearward kick in mid-swing to provide that resistance to mid-swing flexion control, which is naturally not possible, or likely to provide an ungainly spectacle. In the alternative there is no mid swing flexion control against excessive knee flexion seen in so many prosthetic devices in mid-swing.

Further, Yuichi employs the AP plane as per AP plane of the knee device as a means of control, using hip extension and hip flexion forces to control the knee joint's operational characteristic. When the ground reaction force, (a mixture of body weight, resisted body momentum when touching the ground, and any voluntary and involuntary muscle actions) passes the knee joint perpendicular to the controlling AP plane, the behavior of the knee device is either indeterminate, or biased by a resilient element, whereby, for example to maintain a level of resistance low unless the resilient element is compressed by hip effort and, thus, make the behavior of the knee device more predictable. However, for individuals with a short transfemoral stump, the precise control with respect to the resilient element is difficult at best, taking into account the characteristics that if the device can be set such that the required force to control is the same as the force returned by the controller, and that individuals with short transfemoral stumps often have limited strength in their leg stump to control a distal device.

With reference to FIG. 1$iv$, which shows a Pedottii Diagram (commonly referred to as the "butterfly diagram") and FIG. 1$iii$, a GRF is initially tilted backwards, more or less in line with a limb. The body is naturally stable if the GRF passes anterior to the knee center, but the "AP" force vector from the GRF, is oppositely directed with respect to the hip's "AP" force vector and in this scenario the "AP" force vector as per Yuichi would force the knee into stability, which would be undesirable. In the event that the GRF vector passes posterior to the knee axis, then the "AP" force vector-set of shin-and-hip would be opposite and would permit the knee to bend, since the knee would react as if the hip was driving the leg forward. This would result in an immediate knee collapse, followed by a rapid transition to a posterior direction of the "AP" force by the hip and the knee would find stability again and a fall would be arrested, but all at a cost of unstable performance.

FIG. 1$iv$ is a graph that illustrates mean anteroposterior (Fx) GRF component waveform exerted by right and left legs (dotted line) in walking at normal speed. It can be determined that the AP force, in early stance, acts in a backward direction so as to provide a braking action on the body. As would be apparent to a skilled man, this would cause the teaching of certain prior art systems (e.g. Yuichi) teaching to create a free knee joint, which is contrary to the desired response. In late stance the body propels itself forward, but in this stage the knee is inherently stable since knee hyperextension is naturally prevented. It is believed that isolation of a single force "AP" component has not been shown to be sufficient for the control of a prosthesis.

In another prior system—per Blatchford (GB2328160A)—a device is disclosed with an axis proximal to the knee center, which suffers similar logical conflicts as with the teaching to Yuichi with a force-sensing element proximal to the knee center to assist in the control of resistive behavior of the control apparatus distal to the knee center. A device like Blatchford relies on force vectors to pass posterior to the auxiliary axis to generate a desired compression force in an associated sensor, which sensor will in turn switch on the resistance in the distal apparatus. While the sensor is proximal to the knee center, the actual controlling apparatus is distal to the knee center, which is a general conceptual drawback as indicated in the state of the art. In any event, electrical signals from the sensor are processed in terms of signal strength and duration to provide the microprocessor with information relating to the desired response. The sensing of a bending moment related to loading of the limb may be performed by means of a force sensing resistor mounted between, for example, relatively movable parts in the region of the knee joint, and a particularly preferred arrangement is to place the force sensing resistor between, on the one hand, one end of a lever arm the other end of which is pivoted on a knee chassis member forming part of the thigh part of the prosthesis, and, on the other hand, a resilient element inserted between the lever arm and the knee chassis to provide small amounts of flexion independently of the knee flexion control device. Other transducers may be used for producing an electrical signal, which is wholly or partly a function of the knee bending moment.

Blatchford clearly indicates a that a means is sought to determine a level of strain around the knee center to provide the controller with required information of the degree and duration of force, and feedback between resistive force output by the hydraulic controller, so that deviations from the desired levels can be used as input for changing the hydraulic controller's output by altering the state of stepper motor driven valves. The sensor in Blatchford is part of an integral electronic control system wherein the sensor provides feedback with regards to the system's response primarily to its own. Further, the specification of Blatchford provides a clear limitation of operability between 0-35° (GB page 2, 11.22-25), which is believed to arise, at least in part, from the nature of the reaction forces in hydraulic systems and the limitations placed on linear transducers: when the knee bends under resistance over a certain angle; not only does the mechanical leverage over the knee increase with progressive knee angle increasing signal strength in Blatchford's sensor, but also the shortening lever arm for operating piston with increasing knee flexion requires an ever higher hydraulic pressure inside to produce resistive bending moment to the knee. Certainly, using a system in accordance with such teaching, with a sensor in the knee region, will not allow operability of the hydraulic actuator in a meaningful way. This makes the relative placement of any sensor material and a better placement of sensor distinct if it can add new functionality. It is noted that the approach to placement of a sensor in an otherwise comprehensive specification appears to be quite random, nor are the ramifications mentioned.

In a specific example, in the event that a strong force is generated by a forward swing, inertia arising from a distal element will increase the mechanical force sensed by the sensor, and result in an over-estimate of the level of damping required, which would then reduce its resistance to balance the system response, making the response of the prosthesis too weak. Similarly, upon descent of a slope, a hip extension in a weight bearing condition will necessarily result that could cause an increase or decrease in the level of the force determined by the sensor, in dependence upon a momentary angle of knee flexion, and this would necessarily influence the information received by the electronic system. Certainly, using a system in accordance with such teaching, with a sensor positioned adjacent the knee (to minimize the above mentioned disadvantages in relation to stump generated forces affecting the sensor signals that are likely to register knee bending moments), will not allow efficient operability of the hydraulic actuator if sensor is placed remote from the knee center. In fact, if same anterior auxiliary axis and posterior sensor were place more proximal, then hip extension moment would cause sensor to be in tensile mode instead and not represent the moment about the knee joint it is meant to represent as a compressive force signal. The ability of reflex muscle actions to upset signal processing and knee behaviour is a disadvantage present invention seeks to avoid. This makes the relative placement of any sensor material and a better placement of sensor distinct if it can add new functionality. However, such an approach to placement of a sensor in an appears to be at odds with the other ramifications of the specific teaching mentioned in this document.

In another example, concerning the so-called Total Knee by Ossur, a linear damper is placed just proximal a pivot arrangement of a polycentric mechanism. In this knee, the true center in the swing phase the instantaneous center of rotation, which is proximal to the center of mass of the knee joint, as can be determine with reference to a 2007 paper by the "Ossur Academy" entitled Gait training and Prosthetic Knees" by E Kennedy and F Barnett. This paper shows that the linear damper of the Total Knee moves with the thigh element, and in that sense does not control its own inertia, but as a modular joint, its center of mass is distal to the effective knee axis at all times during swing and thigh element does not affect the state of operation of the damper.

The present invention seeks to provide a solution to the problems addressed above: problems associated with moment of inertia of the prosthetic knee device, the need to switch operational modes of the knee in response to ground reaction forces and body reflexes over a full range of knee flexion. The present invention seeks to provide an improved mechanically operated prosthesis for a short stumped femoral amputee, where 'short stump' is intended a length short enough to locate the center of mass of the knee joint and its main operable components proximal to the knee center. The present invention also seeks to provide an improved electrically operated prosthesis for a femoral amputee.

The present invention further seeks to provide a device that is commercially and clinically relevant, and that adequately deals with the problems apparent in respect of certain prior teachings of the art. The present invention further seeks to provide a response independent of a level of anterior-posterior force, as determined by some proponents of the art, with respect to a level of resistance as experienced by the prosthesis.

SUMMARY OF THE INVENTION

Accordingly, the inventor has conceived and reduced to practice, in a preferred embodiment of the invention, an improvement in or relating to prosthetic joints.

In accordance with a general aspect of the invention, there is provided a knee joint with a first member that by mechanical fixation of other members forms a shin and foot component that operate as one unit with respect to the functioning of the knee joint, and first member pivotally connected to a thigh member, connection being the effective knee axis, and first member also pivotally connected to a damper on its one end offset from effective knee axis to provide a lever arm for the damper, and the damper pivotally and proximally connected to the thigh member, such that three pivot connections form a triangle, with damper member of variable length in accordance to its function, and operable to allow knee flexion to take place, and a third member pivotally connected to thigh member, pivotal connection advantageously placed proximal posterior to the effective knee axis, and third member being fixed to the stump, and permitting very limited but distinct movement of third member relative to thigh member, and wherein on hip extension and on presence on ground reaction force passing anterior to the the proximal posterior pivot, the third member moves towards the thigh member to prime a valve in the damper into a state of high resistance, and damper having means to maintain valve closure during the state of high resistance independent on continued or discontinued presence of the priming movement, wherein it is a distinct feature that the operable damping instruments contained within the knee joint does not control its own kinematics of its own moment of inertia.

By the provision of a hybrid construction in having both a mechanical resilient member as well as a piezoelectric, electromagnetic, electrostatic or magnetic force acting on the same moveable skirt of the valve can have advantages: the resilient member can take responsibility for the normal function of the valve, having a passively determined dynamic response of the knee joint as disclosed in, for example, U.S. Pat. No. 8,915,969, and therefore not requiring electrical power for total movement control, which electrical power needs to be provided by some power source, such as a battery of electrical storage cells, but with the added advantage of fine tuning control of the magnetic force or other known means of creating forces by electrical means such as electrostatics and piezoelectrics. The present invention can thus utilize an electrical measure of a rate of change of flexion as a source of system control upon a hydraulic valve, whereby to enable a variation in a pressure differential across a valve and thus to improve, in the case of a prosthetic leg, stumble recovery on the one hand and on the other hand to enable a variation in damping control to enable stability of use, irrespective of rate of a user's gait.

While the present invention can be provided with sensors and functions to identify ground reaction force vectors passing anterior to a virtual reference point in a similar region as the proximal posterior pivot to similarly be employed to allow a damper to switch state of operability which control the damper units, it is preferred that the present invention operates as a weight activated knee joint but does not operate in a default stance mode; that is to say that the prosthesis is preferably characterized such that body weight needs to be applied to activate a high resistance mode, whereby to stabilize the knee joint.

Preferably, the present invention allows not only body weight to activate the stance mode, a hip extension effort exerted on the socket will also activate the stance mode in lieu or in concert with the bodyweight applied to the artificial limb, and hip flexion effort will reduce or negate body weight effects on its mechanism. By this concept, the swing initiation, associated and initiated by hip flexion can overcome any stabilizing effects associated with any residual bodyweight applied, and allow the default low resistance mode to permit the swing phase to take place. Conveniently, as the reference point for operating state of damper is posterior proximal in the knee joint, either a real pivot or a virtual electronic reference point calculated from strain gauges, a hip flexion in combination with weight relief from the prosthesis will cause the ground reaction vector to pass posteriorly to the reference point (axis) prior to passing posterior to the knee axis, such that the damper is brought into a state of low resistance motion before any fluid flow within the damper commences, which in case of high resistance mode would maintain high resistance due to positive feedback to damping state within the damper mechanism. On heel strike in the normal mode, the weight applied on the prosthesis, as well as the hip extension effort will cause the default swing mode to be switched to the weight activated/hip extension activated stance mode. Thus the present invention also provides an activation mechanism for a stance mode by virtue of thigh/hip extension.

Specifically, in accordance with the invention, there is provided a prosthetic limb for fitment to a transfemoral amputee—a person having a thigh-stump that is moveable about their hip, to enable movement with respect to a ground support surface, the prosthetic limb comprising a thigh element, a knee element and a shin element, wherein: the thigh element has a length and is operably connected at a proximal end thereof to the stump of the amputee by means of a stump receiving element and which is pivotally connected at a distal end to a shin element by means of the knee element; the shin element has a length and is operably connected at a proximal end to the thigh by way of the knee element and a distal end thereof, in use, bears upon the ground support surface; wherein the shin element is pivotally connected to the thigh about a knee axis of the knee element; wherein movement of the shin element with respect to the thigh element about the knee axis is operably controlled by a damper element wherein the damper is located between the knee and the stump receiving element, being pivotally mounted with respect to the thigh element at a proximal end thereof and is pivotally connected at a distal end to the shin element at the knee, offset from effective knee axis to provide a lever arm for the damper, whereby to enable control of movement of the shin element with respect to the thigh element about the knee axis.

In use, with a person having a thigh-stump that is moveable about their hip, to enable movement with respect to a ground via a shin element associated with the prosthetic which in use, bears upon the ground support surface. The shin element is pivotally connected to the thigh about the knee axis of the knee element and movement of the shin element with respect to the thigh element about the knee axis is operably controlled by the damper element, whereby to enable control of movement of the shin element with respect to the thigh element about the knee axis. Conveniently, the shin element has a foot element operably associated with the distal end, being connected by way of an ankle, which preferably provides a limited extent of movement.

In accordance with another aspect of the invention, there is provided a transfemoral amputee prosthetic knee joint having a center of mass; wherein the prosthetic knee joint comprises a thigh element, a knee element and a damper; wherein the thigh element is provided with a proximal attachment device, whereby to attach the prosthetic knee joint to an amputee stump interface; wherein the knee element provides an effective knee axis distal to the center of mass of the knee joint, throughout its range of movement, to allow movement of the knee element about the effective knee axis relative to the thigh element and wherein the knee element is provided with a distal attachment device whereby to enable attachment with respect to a shin and foot of prosthesis; wherein there is a damper associated with the thigh element to provide at least a bimodal level of control to movement of the knee element relative to the thigh element; and, wherein the damper has a mass with a center of mass being proximal relative to the knee center; whereby the damper is operable to provide control to movement without substantially affecting the proximity of the mass of the prosthetic knee joint to the amputee stump interface throughout the range of operation of movement. Accordingly, by arranging the damper with the thigh, the change in the component of inertia arising from the damper as it operates is minimal with respect to sum inertia of the prosthetic knee joint.

Accordingly, the present invention overcomes the shortcomings of the prior art by reacting to the ground reaction force as opposed to a single directional component of the force, and that is materially different and distinct. Instead a mid-thigh prosthetic flexible or hinged region is provided in present disclosure that is placed such that a ground reaction force passing posteriorly, causes the mid-thigh-hinged-region to flex (direction of flexion as direction of knee joint flexion), vice versa a force vector passing anteriorly to the mid-thigh-hinged-region causes it to extend (direction of extension as direction of knee joint extension). In this fashion the sense of movement of the mid-thigh-hinged-region is representative of the sum of any anterior—posterior movement/force vector and body weight movement/force vector. Indeed, present disclosure does not use "AP" force as the operating primer for knee joint behavior.

The present invention can thus provide a smooth operational function and there is no graduated control over the state of the knee device in present invention. The mid-thigh-hinged-region reacts purely on the direction and path of the ground reaction force, and its location is chosen such that the ground reaction force will always pass anteriorly during heel strike, mid stance and only during toe-off, when the weight of the user is withdrawn from the limb and hip flexion commences that the mid-thigh-hinged-region to flexes to release the hydraulic damper from an activated high resistance back to a low level of resistance. In this way erratic hip flexion effort in the presence of excess residual body weight on the limb cannot cause the knee to become unstable.

Indeed, in the present invention there is complete a separation between control of resistance and the on-off state of the type of resistance. In present invention the stance resistance is distinct in character and state to the resistance to swing, and the switching between states is controlled by the forward or rearward passing of the ground reaction vector past an auxiliary axis, and seeks no voluntary control: present invention uses the typical ground reaction forces and reflexes as occur in normal amputee gait, and these without any voluntary effort.

It is preferred that the knee joint operates as a weight activated knee joint. Conveniently, the damper is a hydraulic damper. The damper movement in one embodiment is wholly arranged proximate (i.e. as close as possible to) the stump receiving portion of the prosthesis, and substantially proximal to the effective knee center, with a mechanical movement transfer mechanism operable to transfer pivotal movement from the knee axis to a second pivot element proximate the stump receiving portion, the distal portion of the damper being connected with the second pivot portion. In the event that the damper is a linear hydraulic damper it can be operably mounted perpendicularly to an axis of the thigh, with the mechanical movement transfer mechanism comprising one or more of the following: a connecting rod, a chain, a wire and a roller/gear assembly, whereby pivotal movement of the knee axis is translated into a reciprocating linear and/or pivotal movement proximate the stump receiving portion of the thigh. The knee joint can also be of polycentric design if its center of mass is proximal to the effective or virtual or instantaneous knee center (as defined in full extension of the joint).

In accordance with another embodiment of the invention, the prosthetic limb is provided with a thigh element which further comprises an electrical circuit with strain gauges and means to control the damper, the strain gauges being placed on anterior and posterior aspects of the mid-thigh such that, in use, they are operable to determine the flexural properties of the prosthesis and, in the event that strain in the posterior strain gauge represents stretch relative to the strain measured in the anterior strain gauge, an electrical signal can be employed to change or maintain a state of the damper, the damper being centered about the knee axis in case of a rotary design or substantially proximal to the knee center, such that the center of mass of the knee joint as a whole is proximal to the knee center.

In accordance with a further embodiment of the invention, the prosthetic limb is provided with a thigh element further which comprises an electrical circuit with pressure/strain sensors and means to control the damper, the pressure sensors being associated with the stump receiving element such that, in use, they are operable to determine the flexural properties of the prosthesis such that, in the event that pressure upon anterior portion of the stump is greater than the pressure upon a posterior portion of the stump, an electrical signal can be employed to change or maintain a state of the damper, the damper being centered about the knee axis in case of a rotary design or substantially proximal to the knee center, such that the center of mass of the knee joint as a whole is proximal to the knee center.

The electrical state of the strain gauge can be employed to control a solenoid valve, whereby to control a state of the damper or to control a magneto-rheological fluid associated with a damper, whereby to control a state of the damper. Conveniently, the shin element has a foot element operably associated with the distal end, being connected by way of an ankle, and preferably, the ankle provides a limited extent of movement, the damper being centered about the knee axis in case of a rotary design or substantially proximal to the knee center, such that the center of mass of the knee joint as a whole is proximal to the knee center.

In a further variation, the knee axis can comprise a compound joint with two effective axes, operable in succession during a pivot movement about the knee. The damper is conveniently provided as a hydraulic damper having a cooperating piston and cylinder assembly, preferably operating in a rectilinear fashion, with the proximal end being pivotally fastened with respect to the proximal thigh section. Thus, the present invention also provides a prosthetic limb with a knee axis, and a proximal shin portion; the knee-cap, to receive a remainder of the prosthesis, comprising merely the shin and foot, with no significant and relatively massive damper elements. The nature of modern modular design of limb prostheses assures that the present invention can be enabled using many elements that are presently used in leg prostheses and thus not only are they generally available, there is substantial know-how associated with their use.

Conveniently, the present invention provides a mid-thigh articulation point, located approximately between the knee center and the anatomical hip, which articulation point provides a coupling for the damper, which articulation point is posterior to the knee axis, such that a line centered from the articulation point, passing through the knee axis will intersect the foot. Preferably, such articulation point/knee axis line intersects the foot approximately mid-foot. This feature provides a specialized function of a prosthetic knee joint being that of stumble recovery: when the shin extends in terminal swing phase, and if the toe touches the ground, then such a swing may be interrupted and a planned heel strike will not materialize. Instead the toe, the foot, the bent knee and the stump receiving socket will need to be the strut that takes the weight of the patient for a brief moment to allow the other foot—typically a healthy foot—to be lifted off the ground to be positioned such that balance can be restored.

A prosthetic leg with a knee joint is disclosed that offers the benefit of considerably reduced inertia arising from the knee joint and knee joint control system compared with known systems and also provides special benefits with regard to stumble recovery. The benefit arises from an advantageous positioning of components having great mass being placed as close to the stump as possible although not necessarily diminishing the weight of the prosthesis per se. It should be noted that inertial effects of pivotable mass increase in proportional to the square of the distance to the pivot axis, being the hip joint. Putting this in context, in the event that the center of mass of a knee joint can be brought 30.3% closer to the hip joint, then the inertial forces will be reduced by 50%.

In contrast to prior devices, the present disclosure completely separates the response from the hydraulic controller from the ground reaction vectors that control the bi-modal state of the hydraulic controller. This is best illustrated by considering the knee joint to be in a state of flexion of say 90°. A hip extension effort by the amputee using the device of our disclosure, whereas indeed providing a signal to the controller to change state from low level of resistance to high level of resistance, such as to "provide small amounts of flexion independently of the knee flexion control device" the change to high level of resistance in present invention will immediately remove the the "small amounts of flexion" due to the transference of resistive knee movement to the auxiliary axis in present invention causing an immediate small amount of extension, while the controller maintains its state of high resistance through internal means. Sensor or means in our disclosure is a primer for change of state of system from low level of resistance (typically for swing phase) and high level of resistance (typical for stance phase).

It must be understood that with the advancement of modern technology, the prosthesis of present invention may incorporate in a knee joint, with a center of mass proximal to the effective knee axis, microprocessor controlled features such as gyroscopes, tilt switches, GPS positioning systems, reed relays or other means to determine a desired state of operation. Such hydraulic features can also be implemented with stepper motor controlled valves or rheomagnetic fluids. Benefits of the present invention will naturally arise from a proximal positioning of more densely weighted components with respect to a hip of a user. It will be appreciated that the advantages that an amputee will benefit from will be considerable since a knee joint whose movement in swing phase is coupled to the socket attachment and moves with same angular velocity as the socket throughout gait, and which does not independently determine its own inertia is significant.

Present invention is conveniently provided by way of a modular knee joint, meaning that the knee joint is a dismountable and exchangeable part of a whole leg prosthesis, and whereas it is operable to move other parts of the prosthesis such as the foot in mid-swing, and operable to lower the mass of the user's body down a stair, it is a distinct modular device with a proximal and a distal end which are the boundaries of the space envelope of the knee joint per se. Naturally a modular joint, as a product and device, has a center of mass, and prior art modular knee joints have their center of mass distal to the knee center (or knee axis) these are operable about. The weight of a modular joint is frequently declared in the sales literature. Parts of a prosthesis like a foot, shin tube, torque absorbers etc. are referred to as prosthetic components, which are necessary to build a prosthesis, but are separate to present invention. These components need to be moved throughout space during swing phase of the prosthesis, and the precise movement (with particular reference to the angular relationship between these components relative to the stump attachment device) is controlled by the operable means of the knee joint. This operable means of the knee joint has its own center of mass that can be identified in isolation to any housing or exoskeletal part of the knee joint. For the purposes of scope of disclosure, hip disarticulation prostheses will be understood to count as a special form of short transfemoral amputation prosthesis.

BRIEF DESCRIPTION OF THE DRAWING FIGURES

The accompanying drawings illustrate several embodiments of the invention and, together with the description, serve to explain the principles of the invention according to the embodiments. It will be appreciated by one skilled in the art that the particular embodiments illustrated in the drawings are merely exemplary, and are not to be considered as limiting of the scope of the invention or the claims herein in any way.

FIG. 1$i$ shows a prosthesis in a position of a "stumble", a condition that arises in case of an interrupted extension phase of the swing, when the toe catches the ground unintentionally.

FIG. 1$ii$, shows a known prosthesis in a position of toe-off.

FIG. 1$iii$ comprises a skeletal lower body indicating GRF and A-F vectors.

FIG. 1$iv$ shows a Pedottii Diagram, known in the art.

FIG. 1$v$ shows a graph of effective body weight as a function of gait cycle, as is known in the art.

FIGS. 4$i$-4$v$ show key features of various prostheses, as is known in the art.

Figure 5:
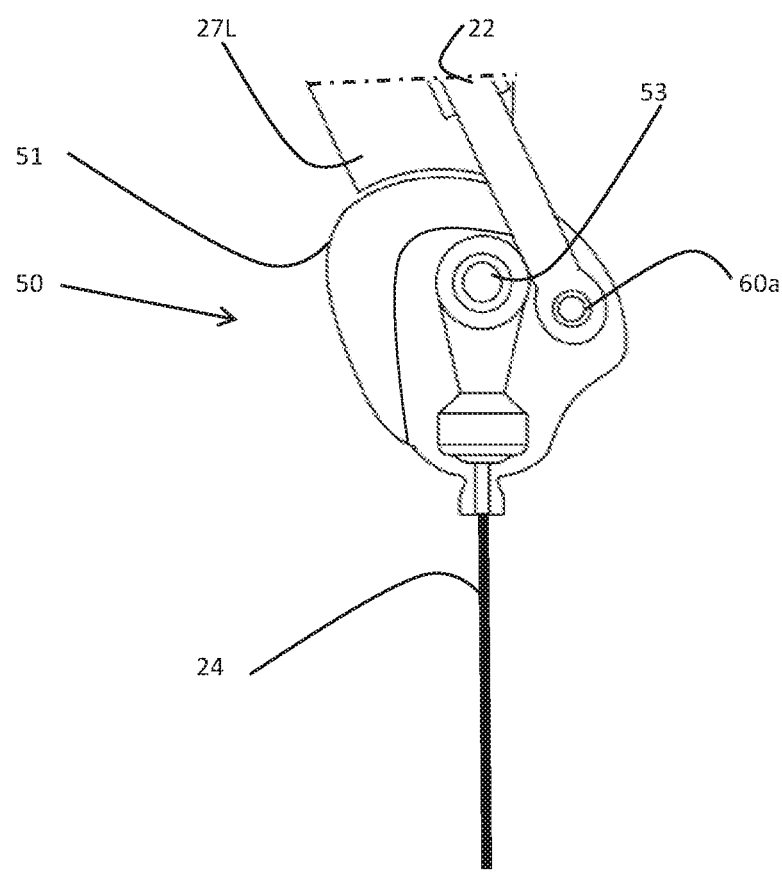

FIG. 5 details a knee of an embodiment of the invention, according to an embodiment of the invention.

Figure 6:
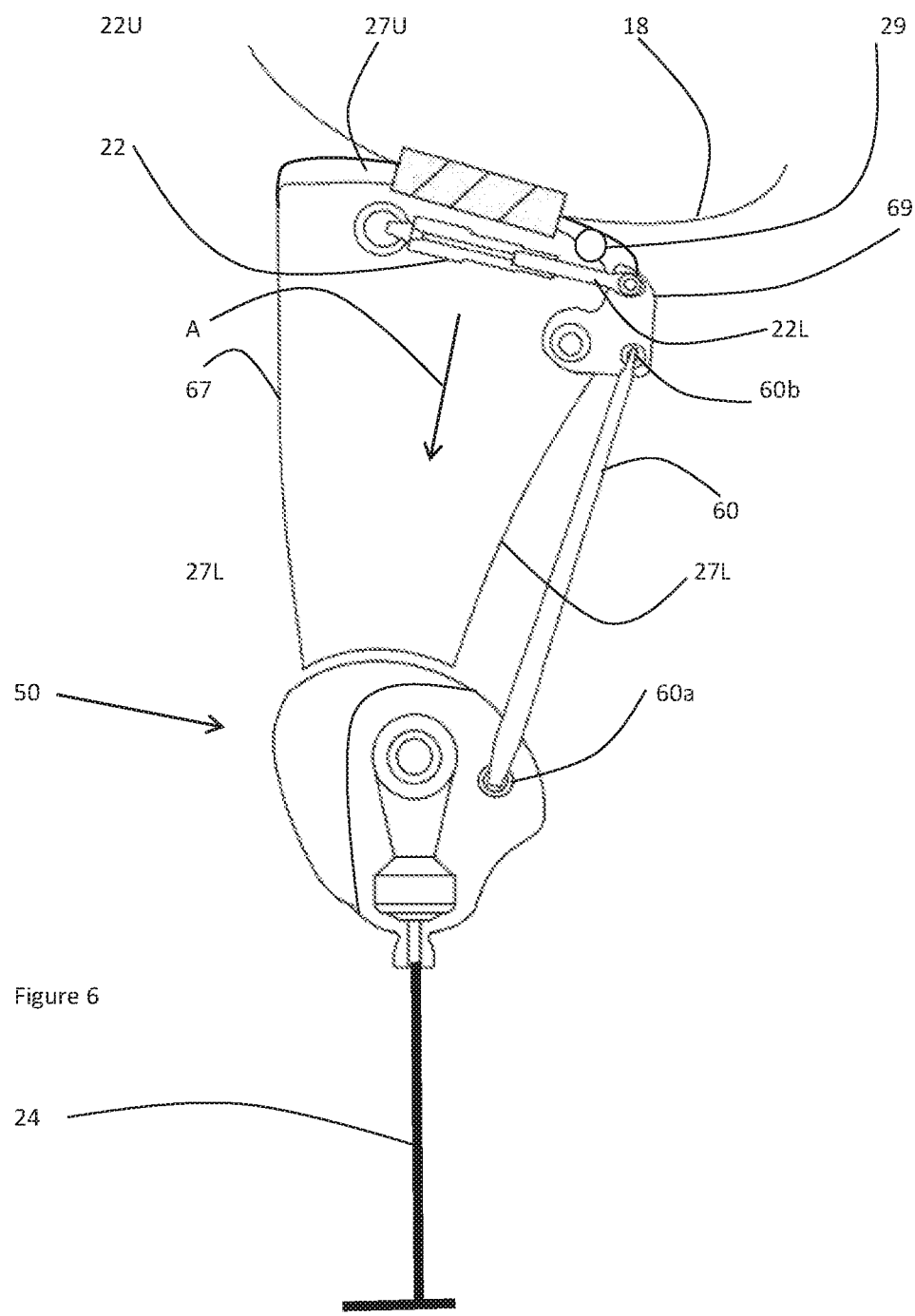

FIG. 6 shows a second prosthetic leg, according to an embodiment of the invention.

FIGS. 7$a$ and 7$b$ show outline comparative features of the prior art with respect to the present invention.

FIG. 7$c$ shows a method to determine location of center of mass of a modular prosthesis, according to an embodiment of the invention.

FIGS. 8$a$ and 8$b$ show how a ground reaction force vector passes through, respectively, a prior art prosthetic and a prosthetic in accordance with the present invention.

DETAILED DESCRIPTION

Definitions

The following terms have specific meanings and it is intended that reference shall be made to this lexicon in event of any doubt:

Hip flexion: when person faces leftwards, a clockwise motion of the thigh, whereas flexion of the knee means an anticlockwise movement of the shin relative to the thigh. A movement about a mid thigh hinge or flexible area to determine direction of strain, needs to be defined for the purposes of consistency, and in this specification the distal half of the prosthetic thigh, when moving in the same sense as the femur moves relative to the trunk will be called mid-thigh flexion. Accordingly, a hip extension effort causes "thigh flexion" if the knee is restrained by force or by inertia. In other words, the movement in association with the mid thigh hinge or flexibility will be of the same sense of direction as the knee joint would be.

Thigh flexion: when person faces leftwards, a clockwise motion of the hip is called hip flexion, similarly when person faces leftwards, a clockwise motion of the distal thigh about a mid thigh flexural region is called thigh flexion for the purposes of this specification. A movement about a mid thigh hinge or flexible area to determine direction of strain or displacement will be called thigh flexion, needs to be defined for the purposes of consistency, and in this specification the distal half of the prosthetic thigh, when moving in the same sense as the femur moves relative to the trunk will be called mid-thigh flexion. Accordingly, a hip extension effort causes 'thigh flexion' if the knee axis is restrained by force or by inertia.

Thigh joint: a flexural or hinged movement within the mid third of a distance between hip joint and knee axis, or such movement purposefully distanced from both hip joint and knee joint to be meaningfully distinct from either in terms of operability of distinguishing force patterns particular to passing through mid thigh region.

Prosthetic leg: a prosthetic leg including a knee joint, also including a hip joint in case of a hip disarticulation prosthesis, in which case, the term transfemoral amputee shall also be assumed to include those amputees having little or no femur.

The terms "proximal" and "distal", as used herein, shall follow normal human anatomy convention, with the head as the base of reference.

DETAILED DESCRIPTION OF PREFERRED EMBODIMENTS

The inventor has conceived, and reduced to practice, in a preferred embodiment of the invention, a hydraulic prosthetic joint.

One or more different inventions may be described in the present application. Further, for one or more of the inventions described herein, numerous alternative embodiments may be described; it should be appreciated that these are presented for illustrative purposes only and are not limiting of the inventions contained herein or the claims presented herein in any way. One or more of the inventions may be widely applicable to numerous embodiments, as may be readily apparent from the disclosure. In general, embodiments are described in sufficient detail to enable those skilled in the art to practice one or more of the inventions, and it should be appreciated that other embodiments may be utilized and that structural, logical, software, electrical and other changes may be made without departing from the scope of the particular inventions. Accordingly, one skilled in the art will recognize that one or more of the inventions may be practiced with various modifications and alterations. Particular features of one or more of the inventions described herein may be described with reference to one or more particular embodiments or figures that form a part of the present disclosure, and in which are shown, by way of illustration, specific embodiments of one or more of the inventions. It should be appreciated, however, that such features are not limited to usage in the one or more particular embodiments or figures with reference to which they are described. The present disclosure is neither a literal description of all embodiments of one or more of the inventions nor a listing of features of one or more of the inventions that must be present in all embodiments.

Headings of sections provided in this patent application and the title of this patent application are for convenience only, and are not to be taken as limiting the disclosure in any way.

The functionality or the features of a device may be alternatively embodied by one or more other devices that are not explicitly described as having such functionality or features. Thus, other embodiments of one or more of the inventions need not include the device itself.

There will now be described, by way of example only, the best mode contemplated by the inventor for carrying out the present invention. In the following description, numerous specific details are set out in order to provide a complete understanding to the present invention. It will be apparent to those skilled in the art, that the present invention may be put into practice with variations of the specific.

Figure 2:
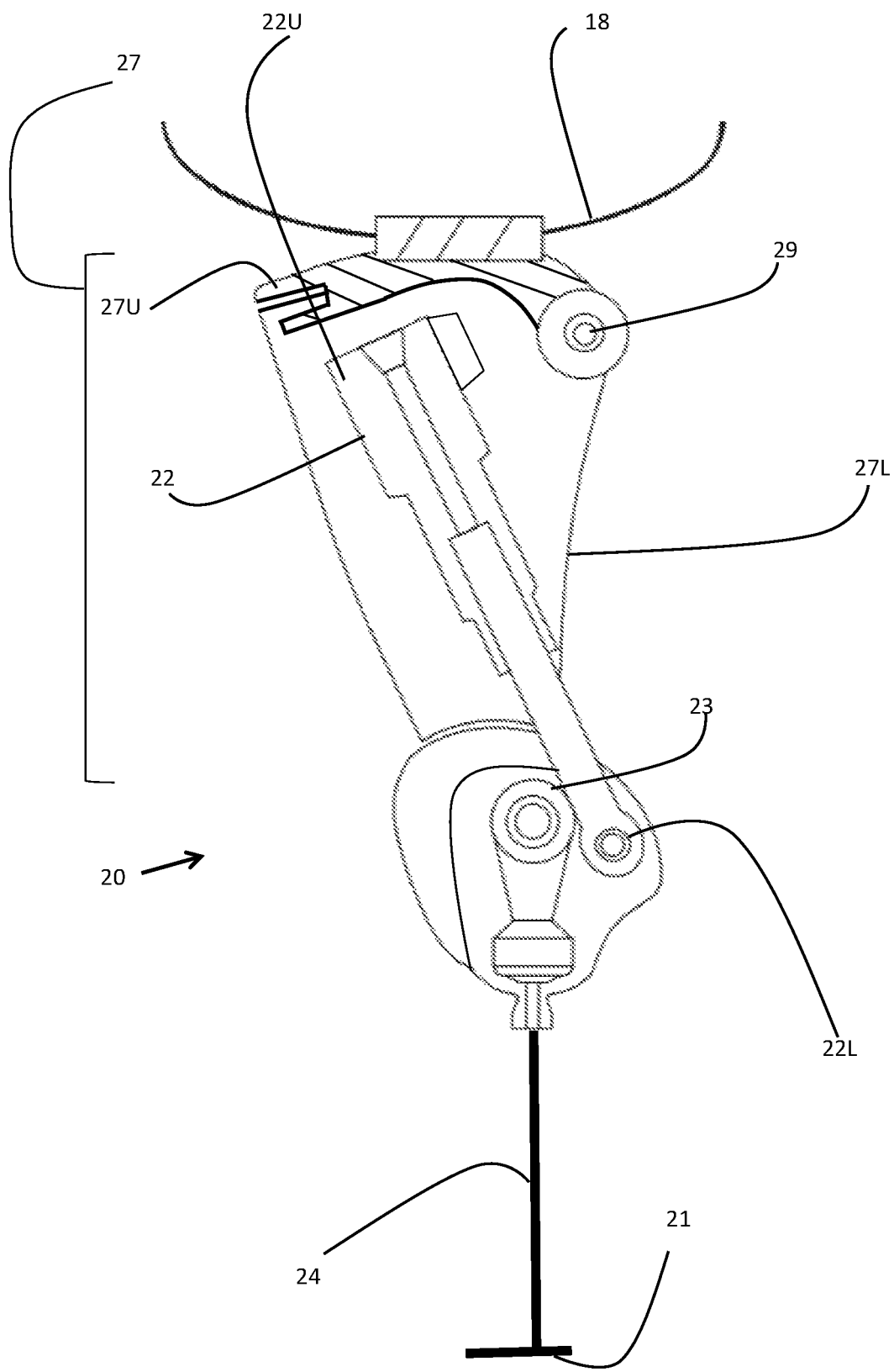
FIG. 2 shows a first prosthetic leg, according to an embodiment of the invention.

Referring to FIG. 2, there is shown a first embodiment of the invention comprising a prosthetic limb assembly 20 comprising a foot element or member 21, a lower leg/shin element or member 24 and a thigh element or member 27. The shin and thigh elements or members are hingedly connected one with respect to the other at respective upper and lower positions (in normal, standing/sitting use by a patient) by means of a knee joint, which pivots about a knee axis 23; a lower part of the shin member 24 is connected to a prosthetic foot and at its top to the knee joint by means of an industry standard pyramid coupling whilst an upper part of the thigh member is connected by similar pyramid coupling system to a stump receiving element or sleeve 18, operable to receive the stump of a trans-femoral patient. Sleeve 18 may also represent a bone anchor abutment. The thigh in this first embodiment comprises two elements; a lower element 27L connected to the knee at a distal end and to an upper section 27U by means of a pivot having an auxiliary axis 29 to allow for a small but operable range (preferably less than 2 degrees) of thigh flexion and extension; the proximal end of the upper element 27U being associated with a femoral stump and or stump receiving element 18. Auxiliary axis 29 allows pivotal movement about itself or, to the same, axis 46 in FIG. 4*iii*, to allow the exposure of strain forces in the thigh element 27 associated with thigh flexion and extension: a difference between a posterior compressive strain and an anterior compressive strain will cause 27U to approach 27L unless the anterior strain is null or tensile. The presence and posterior location of hinge 29 causes a slight difference in apparent functionality compared to the detection of similar strain in the thigh element by means of strain gauges as in FIG. 4*v*, but both systems may make operable the applied weight on the prosthesis as in ordinary weight acceptance in heel strike with a fully extended knee joint, or both systems can make operable a hip extension effort as applied on the stump receiving element 18 (also known as the socket), wherein making operable means the changing of state of the resistance to movement of knee joint by the damper. Since the embodiment can be that of strain gauge to support digital or electrical signal processing, or the embodiment can be mechanical to support direct valve control, the word strain can be suitably interpreted to have the same meaning for any embodiment that makes hip extension operable by making effective the strain in the thigh element. In this embodiment, thigh flexion occurs prior to a change of state of the knee joint and occurs in a state of high resistance. A thigh extension supports a low level of knee flexion resistance depending on the immediate preceding history of knee movement.

A damper 22 is connected at one end 22L to the knee-end of the shin, which rotates about the knee axis with respect to the thigh and is connected at a second end 22U associated with the upper prosthetic thigh element 27U, closely spaced with respect to the femoral stump 18. The articulation point 29 is posterior to the knee axis, such that a line centered from articulation point 29, passing through knee axis 23 will intersect the foot. Preferably, the the articulation point/knee axis line intersects the foot approximately mid-foot. Member 27U pivoting about axis 29 is preferably limited in its pivotal movement to 1-2°, and this movement is preferably cushioned on the ends of the stroke. By positioning the main masses of the artificial limb closer to the remaining part of the femur, the closer the center of the total mass of the leg and prosthetic is to the hip, then the energy required to move the leg is reduced (since the damper does not need to control the movement of its own mass) and the moment of inertia is also reduced (further reducing the repetitive and tiring turnover of kinetic energy by cyclical acceleration and deceleration). The present invention is also distinct in its operation with respect to known systems, taking advantage of the strain forces present in the thigh structure distal to the stump proximal to the anatomical knee center, in fact, proximal to the center of mass of the knee apparatus, center of mass of knee apparatus proximal to knee center 29, to provide benefits in stumble recovery, as shall be discussed below.

Conveniently, the very limited movement of member 27U that is permitted about this mid-thigh articulation point 29 may be used to switch the mode of operation of the damper to enable fluid flow on the application of weight upon the prosthesis, causing thigh extension, in particular member 27U abuts a resilient switch activation element in the proximal part of damper 22. The mechanism within the damper 22 is activated or primed by member 27U, to cause a high resistance function and associated high oil pressure within damper 22. The hydraulic fluid under a condition of high pressure maintains the primed valve in a closed state for the duration of sustained high pressure. This is corresponds to a normal mode of operation, wherein there is a high resistance to bending under body weight bearing after application of body weight on the prosthesis. In fact, after priming of the damper, member 27U discontinues its priming function, as the high resistance condition is maintained. To the contrary, Upon swing initiation, member 27U moves away from frame 27L, whereby to ensure that the damper valve is not primed, whereby there is a reduced resistance to bending, enabling swing phase. In the event movement of the socket during the swing such that the prosthesis is urged forwardly, is reversed by sudden thigh hip extension, then the valve of damper 22 can be activated at any time through thigh flexion to reduce movement and prevent collapse. Specifically, under conditions of heel-strike, a ground reaction vector is directed through the heel, and provides a self-stabilizing force if the vector passes in front of the knee center. In the event that the ground reaction passes posterior to the knee center and anterior to the thigh joint center, then this provides an unstable condition; the knee shall become unsupported and shall have a tendency to collapse. By having the body weight acting through the knee, then the ground reaction force acting anterior to the thigh joint will cause the valve to become closed and a tendency to collapse of the prosthesis will be thwarted.

In being positioned above the knee center, the damper contributes to an efficiency of movement, by the expediency of having the center of mass of the prosthetic limb closer to the hip whereby the damper, effectively, only needs to control the movement of the shin and foot and not that of its own mass, allowing a more controlled swing movement since the center of mass of the shin element made of foot 21 and light weight tube 24 will be distinctly further from knee center 23, allowing for more precise movement control with the short residual limb. In the preferred hydraulic embodiment shown above, auxiliary pivot axis 29 is effectively proximal to the knee center, and posterior to the hip knee ankle line in contrast to known systems (as in FIG. 4ii), where the angle between, on the one hand, a plane passing through the knee axis and the auxiliary axis 45 and, on the other hand, a line passing through knee axis and ankle would remain substantially constant, independent of an actual extent of knee flexion. In contrast, and in accordance with the present invention, the angle between the line through knee axis and ankle and a plane through knee axis and auxiliary axis 46, increases proportionally with respect to knee flexion (as in FIG. 4iii). This means that any ground reaction force passing through the knee axis, and any vector force due to the overall weight of the patient weight line passing through the auxiliary axis 46 are offset, which offset provides a lever effect that gives either force the moment to be effective in priming the valve. This offset increases with knee flexion, meaning that with increased knee flexion, less force is required to prime the valve to bring the damper in high resistance mode, and this force may arise from some weight application or be arising from a hip extension effort from the femur in the leg socket. In fact, the ideal embodiment predicts no force is required when auxiliary axis 46 is used, just movement/displacement/angular position! The fact that position is required as opposed to force against resiliency distinguishes this disclosure from prior art that seeks to employ force present proximal tot the knee center to control a knee. Also, it will be evident that any "AP" force generated by the stump will not resolve in a meaningful control since pivot 46 will transfer this force component completely.

When human beings walk, one foot or the other is always in contact with the ground. Each leg is constantly changing state, going from a "stance phase", when bodily weight is supported by one leg and supporting the bodily weight to a "swing phase", when the leg swings through from behind the body until it is in front of the body, so that it is ready for the next step. The stance phase begins with "heel strike," when the heel initially contacts the ground, in front of the body. The foot then transitions into "foot flat," when bodily mass comes over the foot, when the knee is effectively straight. As the body passes over the foot, the heel starts to rise behind the body and then the knee starts to bend. As the tips of the toes are touching the ground behind the body, the stance phase ends and the swing phase begins; the knee continues to bend, the toes come off the ground, and the heel keeps rising behind the body. As the pelvis and thigh move forwardly, the thigh swings from behind the body, passing underneath the body—all in a bent position—and, as the leg swings forwardly out in front of the body, the knee straightens so that upon heel strike, the leg is straight and ready to accept bodily weight. The end of the swing phase is then reached and the stance phase begins again.

It should be quite clear that for a person with a short leg stump, the push power of the residual limb is diminished in a number of ways. Firstly, the mechanical engagement in the socket of the leg is relatively poor, as the short bone is diffusely wrapped in soft tissue such as muscle, fat and skin, leaving poor quality control to the stump. Secondly, the short stump will quickly build up high reaction forces on the distal bone, which by means of pain and friction soon becomes a limiting factor for further movement. Thirdly, in normal walking, the angular travel of the hip is relatively constant and therefore the available 'travel' of the distal stump in an arc about the hip joint is limited. Additionally, it will also be appreciated that the gait will not be natural, which will also have an effect on efficiency.

By way of a detailed explanation, one can simply consider the energy that it utilized in the form of a basic mathematical equation:

$$E_p = e_s * F_p * h * L_f$$

$E_p$=Maximum energy available for swing
$e_s$=Loss factor for poor mechanical connection between femur and prosthesis
$F_p$=Force on distal femur limited by pain
h=Normal range of hip flexion, that when exceeded produces awkward gait.
$L_f$=length of femur available to traverse through arc $_h$ With all legs, natural and prosthetic, energy is required to accelerate a mass of a foot, to accelerate the mass of a shin, to accelerate the mass of a knee joint to commence swing-phase, and then decelerate the same to enable heel strike in the next step. In accordance with the present invention, energy turnover in an artificial limb can be beneficially minimized whereby to improve efficiency and increases the degree of comfort in wearing an artificial limb. It must be understood that an artificial limb can be modeled as a mass that needs to be brought forward by means of swinging action. This incurs a need to accelerate the mass of leg, which means a gain of kinetic energy, and the subsequent deceleration of the same mass means a loss of such kinetic energy. This energy is dependent on the "velocity per distance traveled" profile of the mass. This can be considered as the energy turnover.

Figure 3:
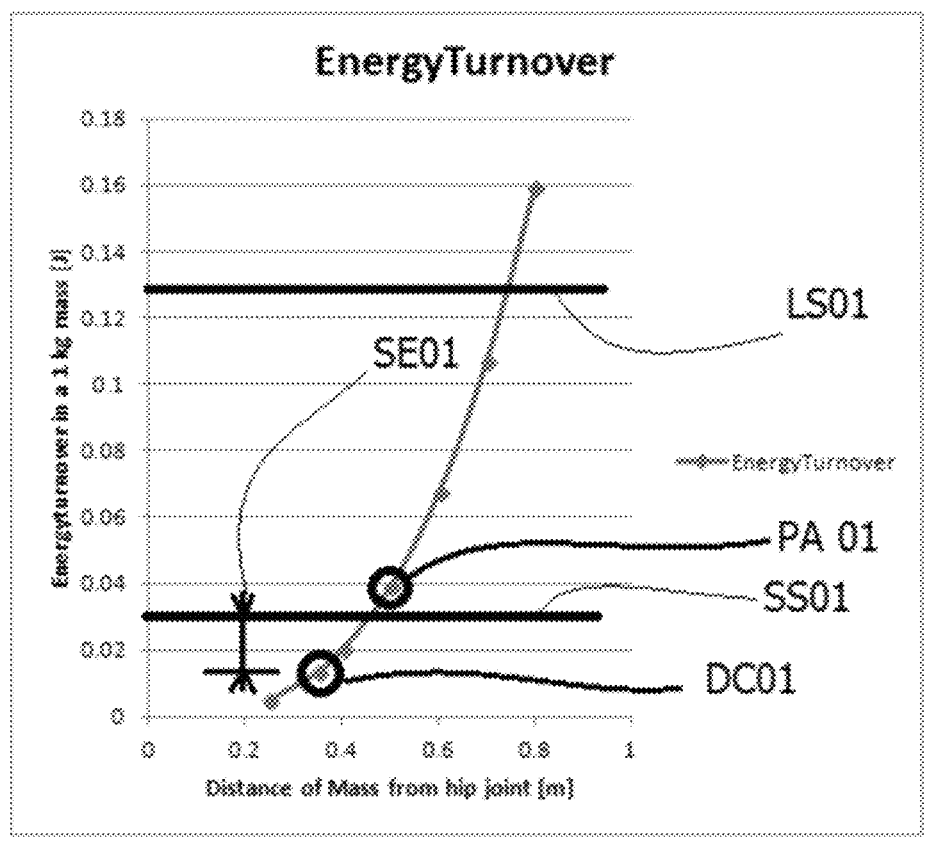
FIG. 3 shows a graph of energy usage versus knee center of mass movement for different prostheses.

With reference to FIG. 3, which is a graph of energy turnover (Y-axis) (arising from the cyclic forces of acceleration followed by deceleration) versus distance of mass center from the hip joint, for a reference mass M of 1 kg (2.2 lb) at a distance L from the hip joint (X-axis) will require at a step length of 0.8 m in 1 sec (standard reference walking speed) in the (simplified condition that the leg is stiff) an estimated acceleration energy turnover, when the arc of motion is limited to 30° for all cases of location of center of mass. With reference to points on the graph, PA01 (Prior-Art 01) is an, estimated reference value of swinging a conventional knee through its arc of swing motion, and DC01 (DiscClosure 01) is the energy turnover for a prosthesis in accordance with the present invention of same mass as that of prior art. The reduction in expended energy using a prosthesis of the present teaching compared to a conventional prosthesis is up to (0.39−0.13)×100/0.39=66%, which is of significant benefit to femoral amputees and the significance of this invention. This is on the basis of moving mass alone. Because the mass of knee as in present invention does not need to be driven forward through a loss making process such as hydraulic damping, further gains in efficiency are obtained, which will further reduce the amount of energy expended, and making available more energy from the stump action to be "utilized for effective kinematic movement". In other words, the stump has to swing a prosthesis forward, which means swinging a foot complex forward and associated knee joint. It will be appreciated that a foot element to the prosthetic would be an independent variable with respect to the invention but, in contrast, the knee is a controllable (dependent) variable.

While known knee joint mechanisms are, in terms of their operable center of mass distal to the knee center, and its associated mechanism require a certain amount of energy from the stump to swing itself forward. This energy is obtained as the residuum of energy put into the damper, and is a function of the damper loss-factor. Since the energy required to swing the mass of the distal center of mass of knee joint is fixed by the kinematics of walking, the loss factor involved from hydraulic dampening acts reciprocally, and becomes a multiplication factor for the force to be generated by the stump. If, as is the case in accordance with the invention, the center of mass of the operable knee joint is proximal to the knee center, then not only does the knee joint take less energy due to diminished acceleration and deceleration in association to hip angle h but also reduces the force amplification factor as outlined above: the stump can swing the operable knee joint mass direct without hydraulic energy loss to be moved through swing. To the contrary, all energy passing out of the damper is fully available to swing the shin and foot complex, which represent mass that from first principle cannot be brought proximal since the foot must be near the ground to act as a foot. As mentioned above, the level of force acting on the distal stump places a limit upon the amount of energy that can be provided to the system, in such a way that a Long Stump may have a high limit LS01, and a will have low limit SS01. These limits cannot be comfortably exceeded. It is noted that previous attempts to make prostheses lighter has involved the use of lighter, but less capable joints, leaving the amputee with a typically poor controllable knee, both in swing phase as well as in stance phase.

It is noted that previous attempts to make prostheses lighter has involved the use of lighter, but less capable joints, leaving the amputee with a typically poor controllable knee, both in swing phase as well as in stance phase. In the graph, the line indicated SE01 is shown the concept of 'reServe' Energy available to the amputee with a limb prosthesis with a center of mass 0.38 m from the hip. This 'reserve' energy is available in case of sudden need without extending beyond the comfort limit SS01. A knee joint with a center of mass positioned in accordance with PA01 chronically exceeds the comfort level SS01, and allows no spare energy to handle special situations. Indeed, to avoid any uncomfortable pressures as per limit SS01, the amputee will have to increase the normal range of motion of hip to possibly 35° or more to increase the arch length of movement and hence reduce acceleration and therefore contact pressures. However this creates inefficient and unsightly body movement.

Figure 4I:
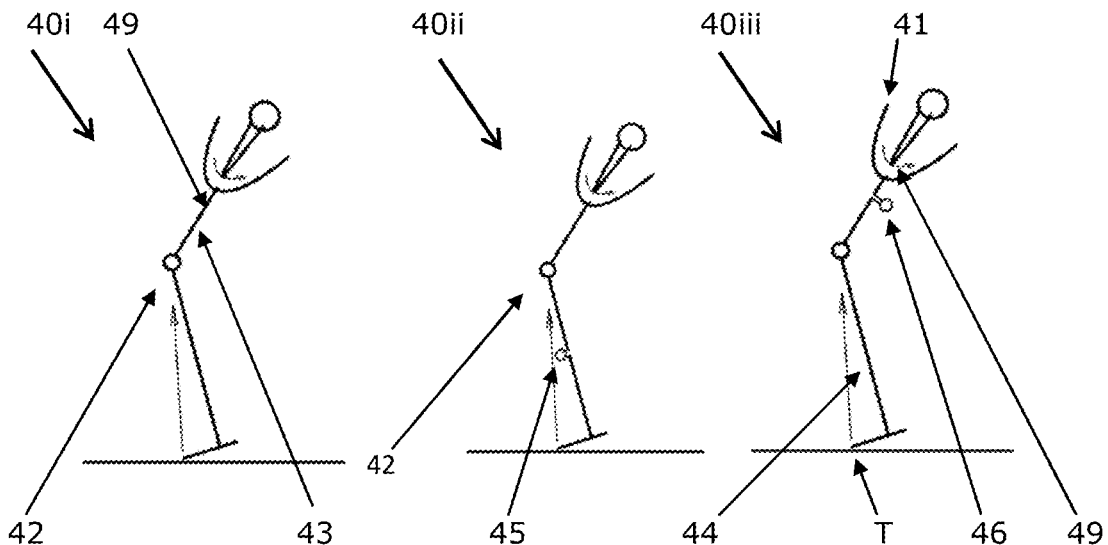

Referring now to FIGS. 4*i*, 4*ii* & 4*iv*, there is a review of prior systems, the new prosthesis 40*iii* being arranged as a weight activated knee joint (otherwise free swinging), wherein the body weight is causing a strain in the resiliency of a member advantageously located between stump socket 41 and anatomical knee center 42, and advantageously closer to the socket rather than to the knee center for reasons that will be made clear below. Naturally any measurement of strain in the thigh structure 43 for an electronically controlled knee joint would need to be positioned as close to the distal stump as possible.

Figure 1I:
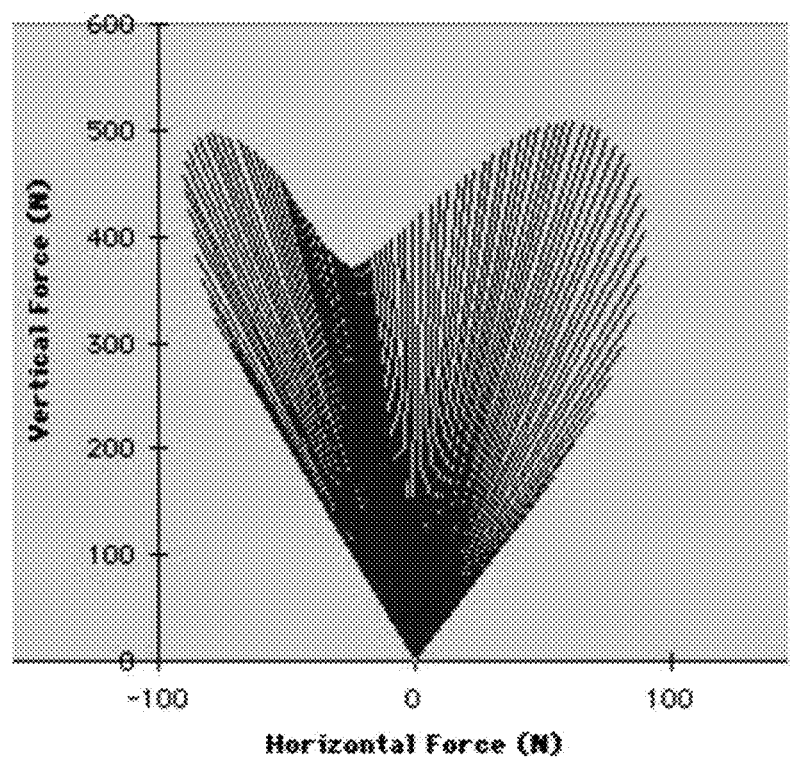
Figure 1V:
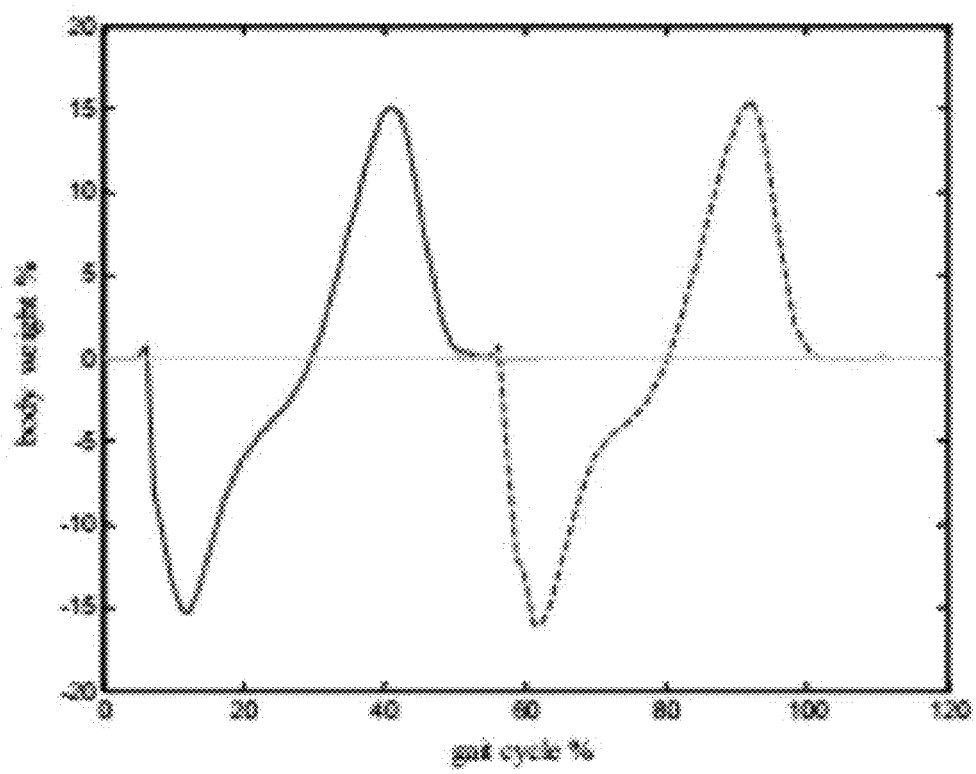

FIG. 4*i* shows a system where there is no provision for stumble recovery. In walking or running a ground reaction force will pass through the low resistance gait being a simple joint). The femoral stump 41 would attempt to resist the forced flexion of the short stump indicated by arrow 49, but would fail for lack of strength. In FIG. 4*ii*, a weight-activated joint is shown, where the joint is brought into weight bearing mode only if the ground reaction force passes posterior to the auxiliary axis 45 of the shin 44, although this is not the case in this prosthesis. This load condition in normal gait is normal for toe-off, and that is when the high resistance surely should not engage (see also FIG. 1*ii*)! So whereas the system shown in FIG. 4*ii* works well in normal gait, in case of a stumble as shown in FIG.

4*ii*, simple mechanical recovery is prevented. FIG. 4*iii*, unlike FIG. 4*ii*, shows a prosthesis with a mid-thigh hinge joint 46 having a limited range of motion (1-2°), conveniently not restrained by a resilient member other than the provision of soft end-stops to the range motion (not shown). The mid-thigh hinge joint 46 would be caused to move under the application of weight upon heel strike and would also be caused to move upon any extension effort in the hip acting on the stump in an attempt to recover from a collapse following a stumble (weight application on the artificial limb prior to full extension). In use, both the ground reaction force (passing through the knee center) and the amputation stump would attempt to resist any forced hip flexion, forced by the shin member pushing onto the knee axis, which would cause the auxiliary joint 46 to close (thigh flexion) and provide signal or priming for a hydraulic knee joint to change state from low resistance to high resistance. However, while prosthetic legs with auxiliary axes are known, they have previously primarily been arranged distal to the anatomical knee axis (FIG. 4*ii*), where resultant forces in use are quite dissimilar to those of the present invention: The loading of the toe in a stumble recovery attempt with such an auxiliary axis 45, or strain gauge 47 as in FIGS. 4*ii* (with auxiliary axis) and 4*iv* (with strain gauge), distal to the anatomical knee center would cause the ground reaction force into the limb at a most unfavorable location, where a weight-activated high resistance mode would be effectively impossible, irrespective of any hip extension effort.

FIGS. 4*iv* and 4*v* show legs suitable for electronic control, in which strain gauges can be provided for electronic control. FIG. 4*iv* shows an example typical of legs produced by Otto Bock in their relatively expensive computer controlled C-leg, where a default stance joint is informed by strain gauge 47 about the ankle. Were this joint to be a free-swinging joint and operate in stance mode by weight activation, as short stumped amputee's desire, then this joint would not offer any stumble recovery. While, the extent of knee flexion could be used as a signal input, such observation is difficult to distinguish from knee flexion at an initial point in the swing phase. In the alternative, as per our disclosure, when such a strain gauge 48 is placed in the mid thigh region, per FIG. 4*v*, then the hip extension moment, or thigh flexion moment can be detected as an input signal for engaging the high resistance mode of the knee joint, even when the knee is flexed, and even if the ground reaction force passes through the center of the knee. It will be appreciated that on toe-off, a hip extension strain will be present in the thigh, which is true. However as the knee can only swing after the ground reaction force passes posterior to the knee center on toe-off, the relative strain in the strain-gauges will be reversed and an associated electronic signal processor will take this into account, noting that in the instance the ground reaction force passes through the knee center, the anterior strain gauge will be in a state of tension relative to the state of the posterior strain gauge which will be in compression, even after taking into account any correction for neutral compression due to residual weight.

By having an auxiliary axis, or strain gauge, in the mid-thigh structure, in accordance with a preferred mechanical version of the present invention, during footfall the ground reaction force entering the fore foot, passes through the knee center forcing the hip to flex, while the hip tends to resist this flexion and in so doing causes a resilient member associated with the auxiliary axis to be compressed, or at least the respect elements of a prosthetic bone to hinge about their auxiliary axis. The compression of the resilient member and/or associated movement allows the activation of a hydraulic circuit closing valve, and the closing of the valve increases the hydraulic resistance of the knee-joint, which tends to maintain a state of closure of the valve via a suitable means of feedback to the valve. By ensuring closure of the valve, in the event that of a sudden increase in flexion resistance, as would be required for stumble recovery, then the forces of compression acting upon the resilient member are reduced.

Figure 4V:
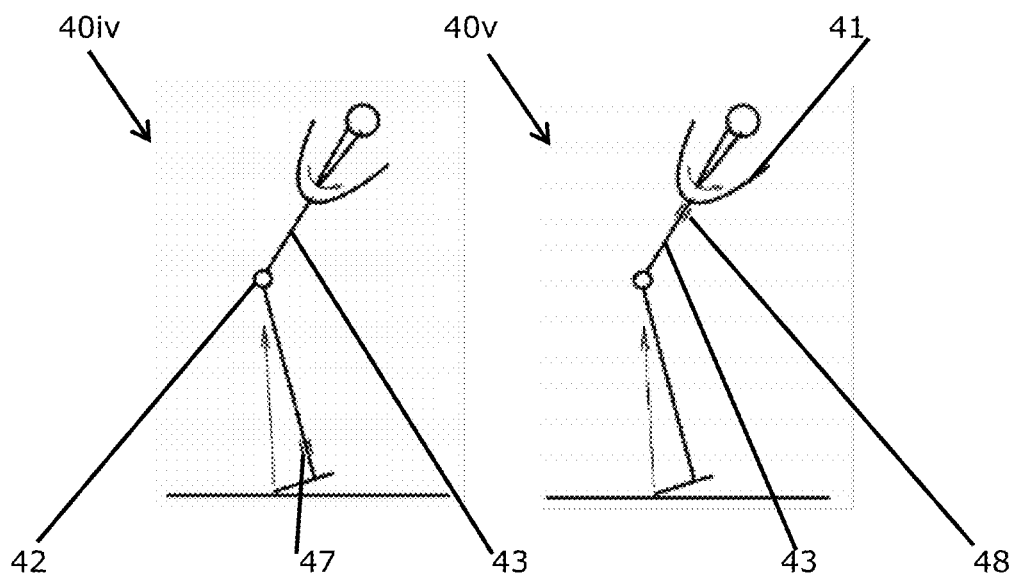

In the event a knee joint of the type as shown in FIGS. 4*iii* and 2, or in FIG. 4*v*, use a strain gauge as input for an electronic alternative of to the control of joint as in FIG. 2, be activated in a stumble, then a state of low resistance to flexion during interrupted knee extension would allow member 27U to approach member 27L, (this is equivalent to the hinge member 46 to close, or for hip 48 to sense a relative posterior tensile stress, a damper as 22 would change state to high resistance, upon which an immediate reversal of the conditions: "allow member 27U to approach member 27L; "allow hinge 46 to close"; or "enable hip 48 to sense a relative posterior tensile stress" would take place, which would be inconsequential to the state of damper due sustenance of the state of the damper for the duration of the high resistance mode.

By having an auxiliary axis, or strain gauge, in the mid-thigh structure, in accordance with a preferred mechanical version of the present invention, during footfall the ground reaction force entering the fore foot, passes through the knee center forcing the hip to flex, while the hip tends to resist this flexion and in so doing causes a resilient member associated with the auxiliary axis to be compressed, or at least the respect elements of a prosthetic bone to hinge about their auxiliary axis. The compression of the resilient member and/or associated movement allows the activation of a hydraulic circuit closing valve, and the closing of the valve increases the hydraulic resistance of the knee-joint, which tends to maintain a state of closure of the valve via a suitable means of feedback to the valve. By ensuring closure of the valve, in the event that of a sudden increase in flexion resistance, as would be required for stumble recovery, then the forces of compression acting upon the resilient member are reduced.

The mechanical construction of an auxiliary axis is advantageous in that it can relatively easily be manufactured and operate with relatively simple, non-electrical system. However, an electrical equivalent can also be provided. For example, an equivalent arrangement utilizing an electrical circuit with strain gauges could determine the flexural properties of the prosthesis about the mid thigh location. Specifically, the set of strain gauges, would be advantageously placed on anterior and posterior aspects of the mid-thigh prosthesis. In the event that strain in the posterior strain gauge represents stretch relative to the strain measured in the anterior strain gauge, even if both would be in compression, then there would be an electrical equivalent to the thigh joint being in a state of extension. The electrical equivalent to sensing state of thigh with respect to flexural tension could then be utilized to control a valve that, in turn would control the state of the damper. A suitably programmed microprocessor could be employed to operate a solenoid driven valve to enable priming of the change in state of the knee joint, to provide a computer-controlled prosthesis. Notwithstanding this, in the limit, the functions of a microprocessor could be replaced by a simple electrical circuit and the strain gauges could be omitted, to be replaced with, for example, an electrical switch associated a thigh plate could operate an electrical switch to be operable to switch the state of resistance of the damper by an open or close valve, or by using a magneto-rheological fluid or other means to the same effect, the common factor in all these alternative designs is the harnessing of the presence of a operable hip or stump effort about the prosthetic knee axis. Indeed this would not exclude the use of any polycentric joint in lieu of the single axis as in the illustrations. Polycentric joints are those where multiple joints are used that together create a virtual center of rotation, or effective knee center, (n.b.: the effective knee center in a uniaxial joint is the uniaxial joint axis) to act as a knee center all the same, and stump effort sensing gauges or operable movements are all anticipated by this disclosure.

It will be understood that for certain persons of a particular weight/stature, a knee joint with a dual axis or polycentric may be determined to provide improved flexibility as shown in FIG. 5, where an exemplary knee is shown generally at 50. The lower leg, the shin 24, together with knee-cap 51 is conveniently articulated with respect to the prosthetic thigh structure 27L, whereby the two prosthetic members act instead of three moveable elements, primarily or reasons of simplicity and reliability. The prosthetic thigh is preferably articulated with the knee cap about a single axis knee center 53; the knee cap also has pivotal attachment at 60a to a piston and cylinder assembly further referred to as damper 22, which damper has its proximal articulation with the proximal thigh. It will be understood that for certain persons of a particular weight/stature, a knee joint with a dual axis or polycentric may be determined to provide improved flexibility.

Turning now to FIG. 6, there is shown a second embodiment of the invention, wherein the articulated prosthetic thigh 67, 27U having an axis 29 to provide a small amount of pivotal movement of the upper unit 27U relative to the lower unit 67. The damper 22 is shown as being oriented effectively perpendicularly with respect to axis A of the thigh. There is a connecting rod 60 fastened at a first, lower end to knee 50 about articulating connection 60a and at a second end to a pivot point 60b, which is mounted upon a pivot member 69, which enables the pivot movement about the knee axis to be transferred to an upper part of the thigh, whereby to further transfer the mass of the leg toward the pivot point of the leg, the hip, further improving the benefits of the invention. Obviously while a simple connecting rod is shown, it can easily be replaced by meshed gears connecting the pivot point of the knee to the pivot point of the lower point of the damper.

Figure 7A:
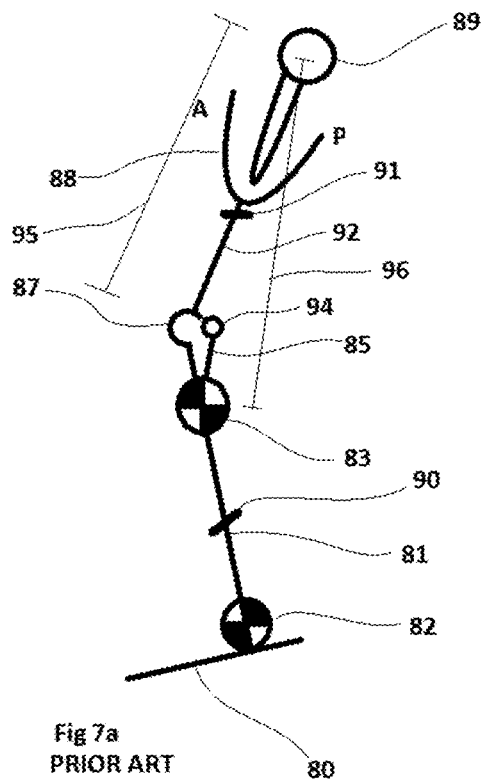

In order to see the advantages of a proximal mass from yet another view, FIG. 7a shows a prior art prosthesis with 89 hip and femur as part of the residual limb contained in socket 88, an arbitrary boundary 91 distal to which there is a knee joint extending to another arbitrary boundary 90 distal to which there is a shin element 81, foot element 80 and inertia of foot and shin 82. Prior art prosthesis has knee joint between boundaries 90 and 91 featuring effective center of rotation 87, whereby effective center 87 may be a distinct knee axis of pivotal nature, or may be an instantaneous knee center known from polycentric knees where the effective knee axis is found by the intersection of the relevant members of the polycentric knee joint, the range of instantaneous knee centers in dependence of knee flexion angle defined as a curve (see good publication made by Van Veen), but for the purposes of this description the range of instantaneous centers of the polycentric joint can be contained in a region 87. Knee joint has center of mass 83 distal to 87, and means 85/94 to mechanically or hydraulically couple members of knee proximal to knee center 87 and distal to region 87, with 94 indicating the location where the resistive torque of the knee joint contained within boundaries 90 and 91 is delivered in case of a piston and cylinder type of damper 85. Naturally a rotary type of damper about knee axis 87 easily replaces damper 85 to no consequence of presentation of prior art. In this prior art prosthesis, the movement in swing is generated by a hip flexing movement and hip flexing moment by 89 that pushes the knee anteriorly A, and inertia 83 and 82 must follow, and follow in a rotary way about knee center region 87, and knee joint between boundaries 90 and 91 shows knee flexion in swing, and movement of knee flexion, and consequently the anterior acceleration of inertia 83 and 82 come about through resistance of damper 85 and the torque 94 it produces. In this way torque 94 must push both inertias 83 and 82 at an energy loss, which is a cost to the amputee and their hip flexion effort.

Figure 7B:
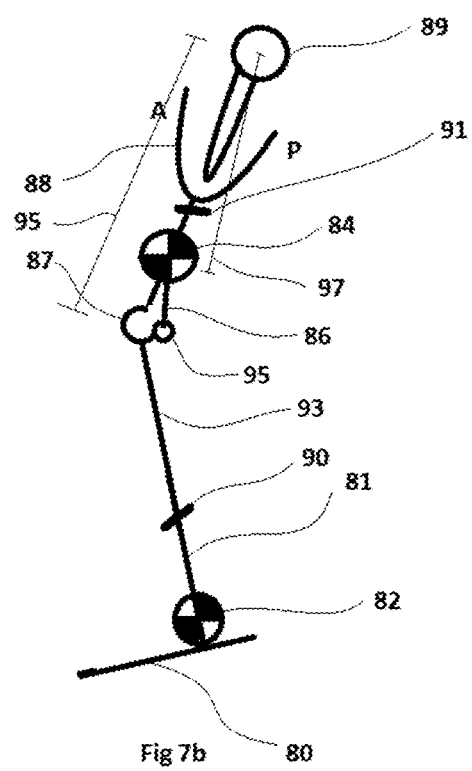

In contrast, FIG. 7b shows a prosthesis in accordance with the present invention, where hip and femur 89, comprising the residual limb bones, are seated within socket 8, connected via knee joint 87 to lower leg (shin) 81 to which foot element 80 is attached. First and second arbitrary boundaries 91, 90 are indicated, respectively, distal to socket 88 and distal to the knee joint. In accordance with the present teaching, the knee joint of the prosthesis features an effective center of pivot 87, whereby effective center 87 may be a distinct knee axis of pivotal nature, or may be an instantaneous knee center known from polycentric knees where the effective knee axis is found by the intersection of the relevant members of the polycentric knee joint, the range of instantaneous knee centers being in dependence of knee flexion angle defined as a curve (see good publication made by Van Veen), but for the purposes of this description the range of instantaneous centers of the polycentric joint can be contained in a region 87. The knee joint has a center of mass 84 proximal to 87, and coupling means 86/95 to mechanically or hydraulically couple members of knee proximal to knee center 87 and distal to region 87, with reference numeral 95 also indicating the location where the resistive torque of the knee joint contained within boundaries 90 and 91 acts in the case that a piston and cylinder type of damper 86 is employed. Naturally, a rotary type of damper about knee axis 87 could alternatively be employed instead of damper 86 with no consequence to the method of operation of the present invention. In this example of prosthesis, the movement in swing can be generated by a hip flexing movement, in particular, a hip flexing moment by femur 89 that pushes the knee anteriorly A, and the inertia of the masses 84 and 82 must follow, mass 84 necessarily follows by reason of the direct connection with socket 88 and mass 82 follows in a pivot fashion about knee center region 87, and knee joint between boundaries 90 and 91 shows knee flexion in swing, and movement of knee flexion, and consequently the anterior acceleration of inertia 82 comes about through resistance of damper 86 and the torque 95 it produces. In this way torque 95 must push only inertia 82 at an energy loss, which is a cost to the amputee and their hip flexion effort, and losses moving inertia 84 are avoided, furthermore it will be clear that prior art (FIG. 7a) inertia 83 is located at a distance greater than distance 95 from hip 89 to knee center 87, and inertia 84 in disclosure (FIG. 7b) is located at distance 97 which is less than 95, and if inertia 83 is taken for the purposes of discussion to be equal to 84, then the force of acceleration of these inertias is proportional to distance 96 squared for the prior art prosthesis, and distance 97 squared for the disclosure prosthesis. It will be apparent by calculated example that if distance 97 equals a 29% reduced distance 96, the force of acceleration by the hip 89 is reduced by 50%.

Figure 7C:
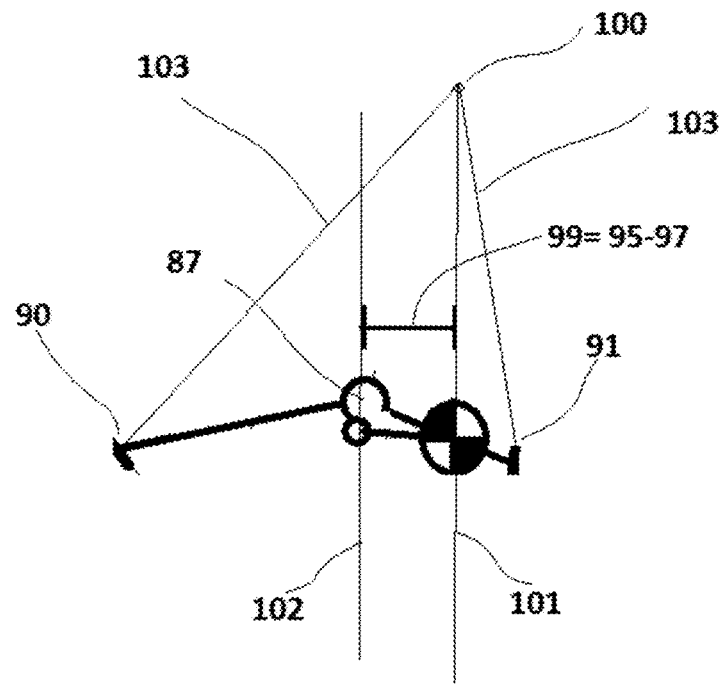

In this discussion in support of a comparison of like with like, the boundaries 90 and 92 that define the knee joint as contained between are truly arbitrary but kept the same, and in case of dispute the knee joint of our disclosure will be defined as a knee joint with all the parts as necessary to remove from one prosthesis to another such as to reproduce the function, inclusive of all accessories like batteries and power supplies and proximal and distal attachments, that by example consist of the typical pyramid connection system as known to those skilled in the manufacture of prostheses, and such knee joint of our disclosure will have a center of mass proximal to the knee center at a distance of at least 10.5% of hip to knee center in the prosthesis, such as to avoid hair splitting discussions with reference to some very small safety knees that may feature a center of mass a few millimeters above or below the knee center. This number of 10.5% represents a ceterus paribus equivalent reduction of moment of inertia by 20%, which is significant enough to be distinct, and 10.5% represents typically 4-5 cm which can be easily determined in a prosthetic workshop as shown in FIG. 7c.

Here, by means of one method, the knee joint as per its own boundaries (terminal ends) 90 and 91 is suspended from these ends by thin cord 103 from a point 100 so that terminal distal end 90 and proximal end 91 are on a common horizontal. The knee joint will be as per our disclosure if the defined knee center 87 is at a distance 99=distance 95 minus distance 97 as per FIG. 7b, being more than 10.5% of distance 95, or in practice more than 5 cm to be distinct from prior art. Further a knee joint in accordance to our disclosure will have it main operable movement control mechanism proximal to the knee center as per common use.

The present invention ensures that, in the event that the ground reaction force passes posterior to the thigh joint—so as to permit thigh movement and thus flexion about the knee—then the body weight for passing through the foot cannot control the valve and bring it to a closed position. However, a reflex action of the stump will urge the ground reaction force to pass in front of the thigh axis, whereby to cause thigh extension, which extension increases with an increase in flexion. While it has been known to allow hip extension effort to arrest collapse, this would purely arise through such an extension and not arise from a specific mode of operation of any hydraulic valve upon the condition of resisted eccentric hip flexion, or resisted concentric hip extension during initiated collapse of the knee joint. Notwithstanding this, the present invention allows the use of thigh extension to arrest further collapse of the knee joint in a condition of partial knee collapse. In the event that the knee joint would suddenly increase in torque resistance, then the inertia arising from the mass of the falling body associated with the artificial limb, would cause the thigh joint to lose its ability to maintain operation of the valve.

A significant problem that the present invention addresses is the functional loss from transfemoral amputation in conjunction with a short bone length. A transfemoral amputation stump can be modeled as a bone-stick in a mantle of soft tissue, all contained in a socket. A well-crafted socket will both maximize the cushioning effect of the soft tissue, as well as minimize the loss of mechanical coupling between femur and socket. This balance between cushioning and firm connection may find a reasonable solution in the mid-length to longer femoral length stump, the same may approach the impossible in the shorter stump. The ratio of bone length and stump diameter becomes very low, which as a consequence cause the distal bone not only to move in an AP direction, but due to the arc-like movement, will also show significant proximal distal movement which causes shear stress in the soft tissue. One observation that has been made is that amputees with short residual limbs frequently select a simple lightweight knee joint that does not provide the functionality that certain modern prostheses provide, but such a choice eliminates the discomfort of having to kick 1.4 kg worth of knee joint into a swing.

Figure 8A:
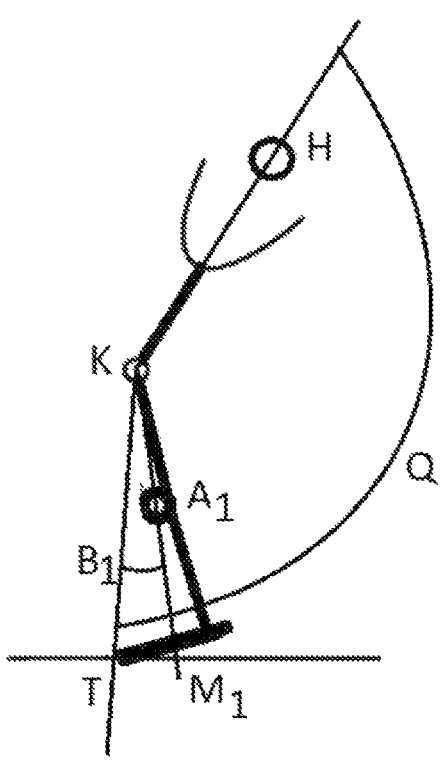
Figure 8B:
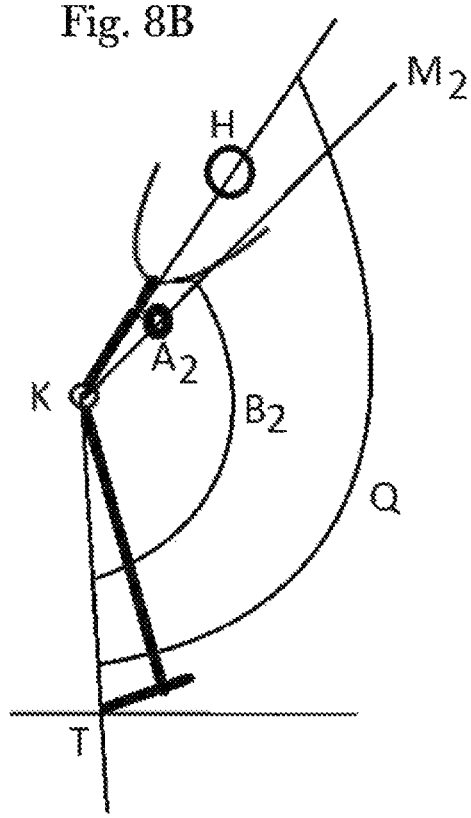

FIG. 8a shows prior art, where a GRF passing through toe T and knee axis K makes a fixed angle B1 with the line of operability through knee axis K and auxiliary axis A1, the angle B1 between T-K and K-A1 remaining constant irrespective of change of knee flexion angle Q between T-K and K-H, (H=hip). This fixed relationship maintains the GRF to pass anterior to A1 with no option for the stump to bring the GRF posterior to A1; therefore stumble recovery is not possible. Referring now to FIG. 8B, which shows an improved arrangement according to the present invention, when auxiliary axis A2 is employed the GRF will pass through T and K, but anterior to A2, a requirement to activate stumble recovery, and as knee flexion angle Q changes so does angle B2 between T-K and K-A2. This makes the hip more enabled to engage high resistance mode by operating A2 by hip extension. This is a distinct difference to prior art.

In view of recent developments to fixing a prosthetic limb to the body, the prosthetic thigh could be connected to a socket that wraps around the leg stump as to connect knee joint to the body, a thigh plate may be provided, which could be fixedly associated with a bone anchor, typically placed percutaneously into the distal femur of the residual limb or stump. Such forms of connection need not be detailed here, but are well known in the field of the invention. Additionally, the present invention can provide a separation between control of resistance and an on-off state of resistance.

In a further variant—and arising specifically from the advantage of positioning the center of mass of the knee joint proximal to the knee center, a less favorable, less desired and stripped down implementation can be provided in a polycentric mechanism, where the body of the knee joint is placed between the distal stump receptacle (socket) and virtual knee center. In this embodiment a severe loss of functionality is encountered as would have been provided by a damper element and damper element must be understood as being replaced by the friction in the device. In this specification a knee joint will be understood to be a modular knee joint as known to those in the art of making leg prostheses, typified with proximal and distal couplings to connect to other limb components in accordance to the choice of medical specification. Therefore the definition of mass distribution of the knee joint will take into account the center of gravity of the knee joint in its decoupled state as prior to be built into a final prosthesis.

The present invention thus provides a prosthetic limb that makes provision for the presence of high torque in the knee joint to maintain valve closure after removal of forces arising from thigh extension, even when thigh extension changes suddenly to thigh flexion upon the knee joint becoming rigid. While the use of forces arising from resistive torque in the knee to maintain a state of valve closure is known, such systems have failed in that they have not supported any priming of the damping valve when a ground reaction force acted through the forefoot, or to be more precise, acted anterior to a curve of intersection of the "plane" through the main and auxiliary axes of the knee joint and the sole of the foot. In the purely mechanical embodiment, when the ground reaction force enters posterior to this curve of intersection, the efficiency of priming such valve is zero when the force passes through the curve of intersection and maximum at the posterior corner of the heel. However, any ground reaction forces entering through the heel and auxiliary axis of prior prosthetic devices couple with an offset body weight force vector passing through the knee center, and the offset provides a force to prime the valve. While this offset does not vary with knee angle, it varies with dependence upon a point of entry of the ground reaction force such that when the ground reaction force enters through or anterior to the intersect curve, the priming is nil or negative. To the extent that proof of benefits are required, Applicant has performed tests and has determined that 1 kg located proximal to the knee center, corresponds by calculation to be 40% lighter than an 850 gram polycentric joint.

In view of recent developments to fixing a prosthetic limb to the body, the prosthetic thigh could be connected to a socket that wraps around the leg stump as to connect knee joint to the body, a thigh plate may be provided, which could be fixedly associated with a bone anchor, typically placed percutaneously into the distal femur of the residual limb or stump. Such forms of connection need not be detailed here, but are well known in the field of the invention. Additionally, the present invention can provide a separation between control of resistance and an on-off state of resistance.

In a further variant—and arising specifically from the advantage of positioning the center of mass of the knee joint proximal to the knee center—a less favorable, less desired and stripped down implementation can be provided in a polycentric mechanism, where the body of the knee joint is placed between the distal stump receptacle (socket) and virtual knee center. In this embodiment a severe loss of functionality is encountered as would have been provided by a damper element and damper element must be understood as being replaced by the friction in the device. In this specification a knee joint will be understood to be a modular knee joint as known to those in the art of making leg prostheses, typified with proximal and distal couplings to connect to other limb components in accordance to the choice of medical specification. Therefore the definition of mass distribution of the knee joint will take into account the center of gravity of the knee joint in its decoupled state as prior to be built into a final prosthesis.

For completeness, the present invention differs from Applicant's prior systems significantly. In a first teaching, Boender provides a weight-activated knee joint, with a chassis distal to the knee center, wherein applied body weight causes a valve to be closed, and the hydraulic pressures within the system upon closure maintain valve closure as long as bending moment on the knee is maintained. Whereas similarities of this concept are disclosed in the present invention, this concept is distinguished from the present teaching on two accounts: namely the hydraulic system is located distal to the knee axis, and this prior art has no means to bring the hydraulic system in a state of high level damping on the occurrence of interrupted swing extension resulting in a stumble when weight is place upon the forefoot (causing to support swing release).

In EP2339995, Boender teaches of a knee joint with fluidic control EP2339995 where in a valve maintains the knee joint in a default state of high resistance, which prior art can only be brought into a state of low level damping upon flexing the knee while weight bearing on the forefoot, which as discussed above is a problem for the short stumped amputee because the hip flexion effort must overcome this residual body weight on the prosthesis to allow swing to commence, and certainly, the center of mass of all shown and specified embodiments is distal to the knee center forcing the situation that the knee joint must not only control the kinetics of the foot but also its own kinematics, which issue is not of concern in the present invention.

EP2478875 teaches of a prosthesis with movement lock, wherein two displacement signals are used to control the state of the knee joint and there is neither any hint nor suggestion to positioning a damper proximal to the knee center nor any form of advantage realized therefrom. Further it relates to a default stance knee joint that on account of two signals permits a low level of resistance to act, whereas present invention requires only one signal to allow the joint to switch states of operability.

The present invention makes provision for the high torque in the knee joint to maintain valve closure after removal of the priming input of the thigh extension, even when thigh extension changes suddenly to thigh flexion after the knee joint has become rigid. The invention provides the amputee with a short stump an improvement that has been overlooked whereby to utilize space for elements used in knee joint control above the main knee center.

Finally it must be understood that, with reference to FIG. 2, damper 22, being associated with the thigh member 27L in terms of being moved together with 27L with the stump and hip of amputee in a synchronised fashion, that the damper has a linear action, and its action is in LINE with the direction of piston action. Any anterior-posterior type of displacement of such damper is not subject to control of the damper because of a nominal friction-less pivot connection with the thigh element, and nominal frictionless connection with the shin element. It can be further shown that in the position of maximum effectiveness of the damper in terms of creating controlling moment is when axis 23 and pivot 22L make an arm perpendicular to the longitudinal axis of the piston damper assembly 22. In this position the full force of the damper is utilised to control distal inertia, whereas the damper will have, in that particular position zero anterior posterior movement, with maximum movement in its axial direction, and damper 22 controls all distal inertia but none of its own (the reactive inertia of the piston rod itself provides part of the controlling force to the distal inertia of shin 24 and foot 21!). Similarly, and in the way cosines and sinus waves oscillate, when pivots 23 and 22L are in line with the longitudinal axis of the piston damper assembly 22, the anterior posterior movement of the damper within the thigh piece 27L is maximum due to rotational movement of shin 24, but no damper movement occurs in the sense of piston displacement, and damper controls no inertia, neither its own. Consequential anterior-posterior movement of the damper is in NO position subject to damper controlling resistance, since all forces resolve in piston-axial force components (controlling only remote inertia) and those perpendicular to the longitudinal axis of the damper (inertia not controlled by the damper). Hence the inertia of the damper is excluded from the inertia controlled by the damper. Were the linear damper placed in association with the shin element, as in prior art, then the damper end connected to the shin element will move at the same angular speed of the knee joint/shin, and be subject to itself in terms of controlling its rotary motion about the knee axis.

In summary, in the prior art, especially a knee joint with hydraulic damping, the center of mass of such a knee joint has been located distal to the effective knee center which causes the center of mass of prior art to be subject to be part of the inertia of which movement the damper is set out to control. One peculiar property of the prior art is that the center of mass on progressive knee flexion comes closer to the amputee stump attachment means, especially with reference to the longitudinal axis of the stump, or alternatively more posterior to the same axis as knee flexion progresses. While this property has not necessarily presented itself as a problem during initial swing, but on extension the problem typically becomes significant, as this mass of knee joint contributes to a momentum that needs to be absorbed by the stump with the momentum approaching from behind the amputation stump, which creates an unstable set of forces, not dissimilar to a ball placed on top of a dome: it can fall either way. In this fashion the momentum from the knee joint often contributes to a gait deviation called 'snaking', where any offset center of mass with impulse causes a momentary twist of the prosthesis, which is unsightly, disturbs the sensory system of the amputee, and can be avoided by bringing the center of mass of the knee joint proximal to the knee center as per present disclosure. The twisting of the limb on terminal dampening due to absorbed momentum causes friction burns, chafing and such ailments commonly known to be part of living with amputation.

It will also be readily appreciated that the invention substantially removes the issue of the gaining and losing momentum in the shin region of the prosthesis by removing mass from that region of the prosthesis, and instead bring as much as possible operable mass proximal to the effective knee joint axis. This arrangement can thus be considered such that the center of mass of the knee joint makes neither significant excursions in a proximal—distal sense with reference to either amputee hip joint, or stump attachment device, or thigh component of the knee joint, nor will there be significant A-P excursion relative to the same on account of the knee joint, and in this way any contribution from the knee joint towards gait deviations on account of momentum absorbed and returned by the knee device is brought to a bare minimum.

For the above reasons, inter alia, the provision of a damper in the thigh complex is believed to have been counterintuitive. Certainly, no such arrangement has been available—even with the history of lower limb prosthetics going back hundreds of years. Importantly, the characteristics of such a joint with the proximal damper, and center of mass of the knee joint as a whole being proximal to the knee center has the great advantages to the amputee as outlined above has neither been suggested nor disclosed. Placing the damper proximal to the knee center is not simply an upside down knee joint, but reflects a new way of teaching transfemoral prosthetics for short stumped amputees, and solutions with relevance to improving life of these individuals.

The skilled person will be aware of a range of possible modifications of the various embodiments described above. Accordingly, the present invention is defined by the claims and their equivalents.

What is claimed is:

1. A transfemoral amputee prosthesis, comprising:
an elongate thigh member having a length with a proximal end and a distal end;
an amputee stump interface assembly connected to the thigh member at the proximal end of the thigh member;
an elongate shin member having a proximal end and a distal end;
a knee member pivotably attached to the distal end of the thigh member and attached to the proximal end of the shin member;
a damper comprising cooperating piston and cylinder elements and having a proximal end and a distal end, the proximal end of the damper being connected to the thigh member and the distal end of the damper being connected to the knee member, the cylinder having a length that is less than the length of the thigh member, the damper being operable to provide control of movement of the knee member; and
an articulation point formed in the thigh member enabling an upper portion of the thigh member to move relative to a lower portion of the thigh member;
wherein movement of the lower portion of the thigh member relative to the upper portion of the thigh member is used to control the damper.

2. The transfemoral amputee prosthesis of claim 1, wherein movement of the lower portion of the thigh member relative to the upper portion of the thigh member in a first direction controls operation of the damper to enable fluid flow within the damper, and movement of the lower portion of the thigh member relative to the upper portion of the thigh member in a second direction controls operation of the damper to disable fluid flow within the damper.

3. The transfemoral amputee prosthesis of claim 1, wherein the articulation point is located proximal to the knee center and posterior to a hip knee ankle line when the thigh and shin members are aligned in a straight line.

4. The transfemoral amputee prosthesis of claim 1, wherein movement of the lower portion of the thigh member relative to the upper portion of the thigh member enables detection of strain forces in the thigh member.

5. The transfemoral amputee prosthesis of claim 1, wherein a range of movement of the lower portion of the thigh member relative to the upper portion of the thigh member is approximately 2 degrees of rotation.

6. The transfemoral amputee prosthesis of claim 1, wherein the thigh member, shin member, and amputee stump interface are modular components connectable using pyramid connection systems.

7. A transfemoral amputee prosthesis, comprising:
a distinct elongate thigh member having a length with a proximal end and a distal end;
an amputee stump interface assembly connected to the thigh member at a proximal end of the thigh member, said amputee stump interface assembly being configured to provide mechanical connectivity to the prosthesis when the prosthesis is in use;
a distinct knee member pivotably attached to the distal end of the thigh member;
an elongate shin member having a proximal end and a distal end, the shin member being configured to provide mechanical continuity from the knee member to the ground when the prosthesis is used for standing, the knee member being attached to the proximal end of the shin member; and
a damper connected to both the thigh member and the knee member, the thigh member operable to provide control over the damper, the damper being operable to provide control of movement of the knee member; the thigh member being configured to be operable by amputee stump hip flexion and extension, the thigh member being configured to act on directional resulting bending moments present within the thigh member during amputee gait;
wherein a center of mass of a combination of the thigh member, the knee member, and the damper, is at least 4 cm proximal to an axis of movement between the knee member and the thigh member throughout any range of angular movement of the knee member;

wherein a sense of direction of proximity has an orientation aligned as being both perpendicular to an axis of rotary movement of the knee member and directed towards the amputee stump interface, whereby this sense of direction with respect to the location of center of mass of the said combination remains after any disassembly of the prosthesis.

8. The transfemoral amputee prosthesis of claim 7, further comprising:
    a first strain gauge on the thigh member to detect forces applied to the thigh member; and
    a control circuit connected to the first strain gauge and configured to use output of the first strain gauge to control the damper.

9. The transfemoral amputee prosthesis of claim 7, wherein the thigh member, shin member, and amputee stump interface are modular components connectable using pyramid connection systems; and
    wherein the knee defines an axis of rotation enabling the shin to pivot in an anterior/posterior direction relative to the thigh member.

10. The transfemoral amputee prosthesis of claim 9, wherein the first strain gauge is positioned to detect posterior/anterior oriented strain forces in the thigh member.

11. The transfemoral amputee prosthesis of claim 10, further comprising a second strain gauge on the thigh member to detect forces applied to the thigh member; and
    wherein the control circuit is connected to both the first strain gauge and second strain gauge and is configured to use output signals of both the first strain gauge and second strain gauge to control the damper.

12. The transfemoral amputee prosthesis of claim 11, wherein the first strain gauge is located on an anterior region of the thigh member and the second strain gauge is located on a posterior region of the thigh member.

13. The transfemoral amputee prosthesis of claim 12, wherein a first combination of output signals from the first and second strain gauges is used by the control circuit to control operation of the damper to enable fluid flow within the damper, and a second combination of output signals from the first and second strain gauges is used by the control circuit to control operation of the damper to disable fluid flow within the damper.

14. The transfemoral amputee prosthesis of claim 7, wherein the thigh member, shin member, and amputee stump interface are modular components connectable using pyramid connection systems.

* * * * *